United States Patent [19]
Draper

[11] Patent Number: 5,972,699
[45] Date of Patent: *Oct. 26, 1999

[54] METHOD AND REAGENT FOR INHIBITING HERPES SIMPLEX VIRUS REPLICATION

[75] Inventor: Kenneth G. Draper, Boulder, Colo.

[73] Assignee: Ribozyme Pharmaceuticals, Inc., Boulder, Colo.

[*] Notice: This patent is subject to a terminal disclaimer.

[21] Appl. No.: 08/835,269

[22] Filed: Apr. 8, 1997

Related U.S. Application Data

[63] Continuation of application No. 08/623,891, Mar. 25, 1996, Pat. No. 5,795,778, which is a continuation of application No. 08/238,200, Jun. 4, 1994, abandoned, which is a continuation of application No. 07/987,133, Dec. 7, 1992, abandoned, which is a continuation-in-part of application No. 07/948,359, Sep. 18, 1992, abandoned, which is a continuation-in-part of application No. 07/882,921, May 14, 1992, abandoned.

[51] Int. Cl.[6] .................................................. C07H 19/10
[52] U.S. Cl. ...................... 435/320.1; 435/236; 576/23.1
[58] Field of Search .................................... 435/236, 326, 435/320.1; 514/44; 536/23.1

[56] References Cited

FOREIGN PATENT DOCUMENTS

| 9104319 | 9/1990 | WIPO . |
| 9115580 | 10/1991 | WIPO . |
| 9200749 | 1/1992 | WIPO . |

OTHER PUBLICATIONS

Taylor and Rossi, "Ribozyme–Mediated Cleavage of an HIV–1 gag RNA: The Effects of Nontargeted Sequences and Secondary Structure on Ribozyme Cleavage Activity," *Antisense Res. and Dev.* 1:173–186 (1991).

Tsukiyama–Kohara et al., "Internal Ribosome Entry Site Within Hepatits C Virus RNA," *Journal of Virology* 66:1476–1483 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Weerasinghe et al., "Resistance to Human Immunodeficiency Virus Type 1 (HIV–1) Infection in Human CD4[+] Lymphocyte–Derived Cell Lines Conferred by Using Retroviral Vectors Expressing an HIV–1 RNA–Specific Ribozyme," *Journal of Virology* 65:5531–5534 (1994).

Zuker, "On Finding All Suboptimal Foldings of an RNA Molecule," *Science* 244:48–52 (1989).

Zuker and Stiegler, "Optimal Computer Folding of Large RNA Sequences Using Thermodynamics and Auxiliary Information," *Nucleic Acids Research* 9:133–148 (1981).

Haseloff and Gerlach, "Simple RNA Enzymes with New and Highly Specific Endoribonuclease Activities," *Nature* 334:585–591 (1988).

Jaeger et al., "Improved Predictions of Secondary Structures for RNA," *Proc. Natl. Acad. Sci. USA* 86:7706–7710 (1989).

Kashani–Sabet et al., "Reversal of the Malignant Phenotype by an Anti–ras Ribozyme," *Antisense Research & Development* 2:3–15 (1992).

Koizumi et al., "Ribozymes Designed to Inhibit Transformation of NIH3T3 Cells by the Activated c=Ha–ras Gene," *Gene* 117:179–184 (1992).

Mamone et al., "Design of Hammerhead Ribozymes Targeted to Sequences in HIV, HSV and the RAT ANF Gene," Abstract of Keystone, CO (May 27, 1992).

*New Riverside University Dictionary*, Houghton Miifflin Co., p. 437 (1984).

Pavco et al., "Regulation of Self–Splicing Reactions by Antisense RNA," Abstract of Keystone, CO (May 27, 1992).

Perrotta and Been, "Cleavage of Oligoribonucleotides by a Ribozyme Derived from the Hepatitis δ Virus RNA Sequence," *Biochemistry* 31:16–21 (1992).

Rossi and Sarver, "RNA enzymes (ribozymes) as antiviral therapeutic agents," *TIBTECH* 8:179–183 (1990).

Sambrook et al., *Molecular Cloning: A Laboratory Manual*, published by Cold Spring Harbor Laboratory Press, New York, New York, pp. 7.71–7.78 (1989).

Sarver et al., "Ribozymes as Potential Anti–HIV–1 Therapeutic Agents" *Science* 247:1222–1225 (1990).

Sarver et al., "Catalytic RNAs (Ribozymes): A New Frontier in Biomedical Applications," *AIDS Res. Revs.* 2:259–285 (1992).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Sioud and Drlica, "Prevention of Human Immunodeficiency Virus Type 1 Integrase Expression in *Escherichia coli* by a Ribozyme," *Proc. Natl. Acad. Sci. USA* 88:7303–7307 (1991).

Slim and Gait, "Configurationally Defined Phosphorothioate–Containing Oligoribonucleotides in the Study of the Mechanism of Cleavage of Hammerhead Ribozymes," *Nucleic Acids Research* 19:1183–1188 (1991).

Cameron and Jennings, "Specific Gene Expression by Engineered Ribozymes in Monkey Cells," *Proc. Natl. Acad. Sci. USA* 86:9139–9143 (1989).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chuat and Galibert, "Can Ribozymes be Used to Regulate Procaryote Gene Expression?" *Biochemical and Biophysical Research Communications* 162:1025–1029 (1989).

(List continued on next page.)

*Primary Examiner*—Charles L. Patterson, Jr.
*Attorney, Agent, or Firm*—Lyon & Lyon LLP

[57] ABSTRACT

An enzymatic RNA molecule which specifically cleaves a herpes simplex virus mRNA molecule.

21 Claims, 1 Drawing Sheet

OTHER PUBLICATIONS

Dropulic et al., "Functional Characterization of a U5 Ribozyme: Intracellular Suppression of Human Immunodeficiency Virus Type I Expression," *Journal of Virology* 66:1432–1441 (1992).

Guerrier–Takada et al., "The RNA Moiety of Ribonuclease P Is the Catalytic Subunit of the Enzyme," *Cell* 35:849–857 (1983).

*Haekh's Chemical Dictionary*, 4th edition, edited by J. Grant, McGraw Hill Book Company, p. 242 (1969).

Hampel and Tritz, "RNA Catalytic Properties of the Minimun (–)sTRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

SEQUENCE LISTING (1) GENERAL INFORMATION:

(iii) NUMBER OF SEQUENCES:   115

(2) INFORMATION FOR SEQ ID NO:   1:

(i) SEQUENCE CHARACTERISTICS:

(A) LENGTH:          22
        (B) TYPE:            nucleic acid
        (C) STRANDEDNESS:    single
        (D) TOPOLOGY:        linear (ii) SEQUENCE DESCRIPTION:   SEQ ID NO: 1:

AGAGACAGAC CGUCAGACGC UC (2) INFORMATION FOR SEQ ID NO:   2:

(i) SEQUENCE CHARACTERISTICS:

(A) LENGTH:          15
        (B) TYPE:            nucleic acid
        (C) STRANDEDNESS:    single
        (D) TOPOLOGY:        linear (ii) SEQUENCE DESCRIPTION:   SEQ ID NO: 2:

CCGGGACGCC GAUAC (2) INFORMATION FOR SEQ ID NO:    3:

(i) SEQUENCE CHARACTERISTICS:

(A) LENGTH:           20
        (B) TYPE:             nucleic acid
        (C) STRANDEDNESS:     single
        (D) TOPOLOGY:         linear (ii) SEQUENCE DESCRIPTION:  SEQ ID NO: 3:

GGAUCGGCCG UCCCUGUCCU                                           20

(2) INFORMATION FOR SEQ ID NO:    4:

(i) SEQUENCE CHARACTERISTICS:

(A) LENGTH:           20
        (B) TYPE:             nucleic acid
        (C) STRANDEDNESS:     single
        (D) TOPOLOGY:         linear (ii) SEQUENCE DESCRIPTION:  SEQ ID NO: 4:

ACCCAAGCAU CGACCGGUCC                                           20

(2) INFORMATION FOR SEQ ID NO:    5:

(i) SEQUENCE CHARACTERISTICS:

(A) LENGTH:           19
        (B) TYPE:             nucleic acid
        (C) STRANDEDNESS:     single
        (D) TOPOLOGY:         linear (ii) SEQUENCE DESCRIPTION:  SEQ ID NO: 5:

GGUCUCGCCC CCUCCCCCC                                            19

(2) INFORMATION FOR SEQ ID NO:    6:

(i) SEQUENCE CHARACTERISTICS:

(A) LENGTH:           31
        (B) TYPE:             nucleic acid
        (C) STRANDEDNESS:     single
        (D) TOPOLOGY:         linear (ii) SEQUENCE DESCRIPTION:  SEQ ID NO: 6:

UAGGUGACCU ACCGUGCUAC GUCCGCCGUC G                               31

(2) INFORMATION FOR SEQ ID NO:    7:

(i) SEQUENCE CHARACTERISTICS:

(A) LENGTH:           13
        (B) TYPE:             nucleic acid
        (C) STRANDEDNESS:     single
        (D) TOPOLOGY:         linear (ii) SEQUENCE DESCRIPTION: SEQ ID NO: 7:

UAUCCCCGGA GGA                                                                                          13

(2) INFORMATION FOR SEQ ID NO:    8:

(i) SEQUENCE CHARACTERISTICS:

(A) LENGTH:           31
        (B) TYPE:             nucleic acid
        (C) STRANDEDNESS:     single
        (D) TOPOLOGY:         linear (ii) SEQUENCE DESCRIPTION: SEQ ID NO: 8:

GGCGUCGGAG AACAAGCAGC GCCCCGGCUC C                                                                       31

(2) INFORMATION FOR SEQ ID NO:    9:

(i) SEQUENCE CHARACTERISTICS:

(A) LENGTH:           12
        (B) TYPE:             nucleic acid
        (C) STRANDEDNESS:     single
        (D) TOPOLOGY:         linear (ii) SEQUENCE DESCRIPTION: SEQ ID NO: 9:

CACGACCUCG AC                                                                                            12

(2) INFORMATION FOR SEQ ID NO:    10:

(i) SEQUENCE CHARACTERISTICS:

(A) LENGTH:           31
        (B) TYPE:             nucleic acid
        (C) STRANDEDNESS:     single
        (D) TOPOLOGY:         linear (ii) SEQUENCE DESCRIPTION: SEQ ID NO: 10:

CGCCGUCUCG CCGCGACAGC UGGCUCUGCU G                                                                       31

(2) INFORMATION FOR SEQ ID NO:    11:

(i) SEQUENCE CHARACTERISTICS:

(A) LENGTH:           21
        (B) TYPE:             nucleic acid
        (C) STRANDEDNESS:     single
        (D) TOPOLOGY:         linear (ii) SEQUENCE DESCRIPTION: SEQ ID NO: 11:

GUCCGGACGA UCCCGACGCC C                                                                                  21

(2) INFORMATION FOR SEQ ID NO:    12:

(i) SEQUENCE CHARACTERISTICS:

```
        (A) LENGTH:             31
        (B) TYPE:               nucleic acid
        (C) STRANDEDNESS:       single
        (D) TOPOLOGY:           linear (ii) SEQUENCE DESCRIPTION: SEQ ID NO: 12:

GACGACGAUG ACGGGGACGA GUACGACGAC G                              31

(2) INFORMATION FOR SEQ ID NO:   13:

(i) SEQUENCE CHARACTERISTICS:

(A) LENGTH:             15
        (B) TYPE:               nucleic acid
        (C) STRANDEDNESS:       single
        (D) TOPOLOGY:           linear (ii) SEQUENCE DESCRIPTION: SEQ ID NO: 13:

GUAUCCGGAC CCCAC                                                15

(2) INFORMATION FOR SEQ ID NO:   14:

(i) SEQUENCE CHARACTERISTICS:

(A) LENGTH:             13
        (B) TYPE:               nucleic acid
        (C) STRANDEDNESS:       single
        (D) TOPOLOGY:           linear (ii) SEQUENCE DESCRIPTION: SEQ ID NO: 14:

CGUCGUCACG GCC                                                  13

(2) INFORMATION FOR SEQ ID NO:   15:

(i) SEQUENCE CHARACTERISTICS:

(A) LENGTH:             9
        (B) TYPE:               nucleic acid
        (C) STRANDEDNESS:       single
        (D) TOPOLOGY:           linear (ii) SEQUENCE DESCRIPTION: SEQ ID NO: 15:

CAUAGACCT                                                       9

(2) INFORMATION FOR SEQ ID NO:   16:

(i) SEQUENCE CHARACTERISTICS:

(A) LENGTH:             13
        (B) TYPE:               nucleic acid
        (C) STRANDEDNESS:       single
        (D) TOPOLOGY:           linear (ii) SEQUENCE DESCRIPTION: SEQ ID NO: 16:

GUCCGCAUCC UCU                                                  13

(2) INFORMATION FOR SEQ ID NO:   17:
```

(i) SEQUENCE CHARACTERISTICS:
        (A) LENGTH:         12
        (B) TYPE:           nucleic acid
        (C) STRANDEDNESS:   single
        (D) TOPOLOGY:       linear (ii) SEQUENCE DESCRIPTION: SEQ ID NO: 17:

GCAUCGAGCG CC                                                           12

(2) INFORMATION FOR SEQ ID NO:  18:

(i) SEQUENCE CHARACTERISTICS:
        (A) LENGTH:         22
        (B) TYPE:           nucleic acid
        (C) STRANDEDNESS:   single
        (D) TOPOLOGY:       linear (ii) SEQUENCE DESCRIPTION: SEQ ID NO: 18:

GGGCCGCUUC ACGGCCGGGC AG                                                22

(2) INFORMATION FOR SEQ ID NO:  19:

(i) SEQUENCE CHARACTERISTICS:
        (A) LENGTH:         18
        (B) TYPE:           nucleic acid
        (C) STRANDEDNESS:   single
        (D) TOPOLOGY:       linear (ii) SEQUENCE DESCRIPTION: SEQ ID NO: 19:

GCGACGCCGG UUCGAGGC             18

(2) INFORMATION FOR SEQ ID NO:  20:

(i) SEQUENCE CHARACTERISTICS:
        (A) LENGTH:         14
        (B) TYPE:           nucleic acid
        (C) STRANDEDNESS:   single
        (D) TOPOLOGY:       linear (ii) SEQUENCE DESCRIPTION: SEQ ID NO: 20:

ACGCCCUGAU CACG                                                         14

(2) INFORMATION FOR SEQ ID NO:  21:

(i) SEQUENCE CHARACTERISTICS:
        (A) LENGTH:         17
        (B) TYPE:           nucleic acid
        (C) STRANDEDNESS:   single
        (D) TOPOLOGY:       linear (ii) SEQUENCE DESCRIPTION: SEQ ID NO: 21:

GGGGUGGCUC CAGAACC                                                      17

(2) INFORMATION FOR SEQ ID NO:  22:

(i) SEQUENCE CHARACTERISTICS:
        (A) LENGTH:         31
        (B) TYPE:           nucleic acid
        (C) STRANDEDNESS:   single
        (D) TOPOLOGY:       linear (ii) SEQUENCE DESCRIPTION: SEQ ID NO: 22:

AACAGCAGCU CCUUCAUCAC CGGCAGCGUG G					31

(2) INFORMATION FOR SEQ ID NO:   23:

(i) SEQUENCE CHARACTERISTICS:
        (A) LENGTH:         13
        (B) TYPE:           nucleic acid
        (C) STRANDEDNESS:   single
        (D) TOPOLOGY:       linear (ii) SEQUENCE DESCRIPTION: SEQ ID NO: 23:

GCCUGGCGCA CGC						13

(2) INFORMATION FOR SEQ ID NO:   24:

(i) SEQUENCE CHARACTERISTICS:
        (A) LENGTH:         12
        (B) TYPE:           nucleic acid
        (C) STRANDEDNESS:   single
        (D) TOPOLOGY:       linear (ii) SEQUENCE DESCRIPTION: SEQ ID NO: 24:

CCGUGGCCAU GA						12

(2) INFORMATION FOR SEQ ID NO:   25:

(i) SEQUENCE CHARACTERISTICS:
        (A) LENGTH:         12
        (B) TYPE:           nucleic acid
        (C) STRANDEDNESS:   single
        (D) TOPOLOGY:       linear (ii) SEQUENCE DESCRIPTION: SEQ ID NO: 25:

AUACGACCGC GC						12

(2) INFORMATION FOR SEQ ID NO:   26:

(i) SEQUENCE CHARACTERISTICS:
        (A) LENGTH:         23
        (B) TYPE:           nucleic acid
        (C) STRANDEDNESS:   single
        (D) TOPOLOGY:       linear (ii) SEQUENCE DESCRIPTION: SEQ ID NO: 26:

GCGCAGAAGG GCUUCCUGCU GAC					23

(2) INFORMATION FOR SEQ ID NO: 27:

(i) SEQUENCE CHARACTERISTICS:

(A) LENGTH: 28
      (B) TYPE: nucleic acid
      (C) STRANDEDNESS: single
      (D) TOPOLOGY: linear (ii) SEQUENCE DESCRIPTION: SEQ ID NO: 27:

GCCUGCCGCG GGAUCCUGGA GGCGCUGG 28

(2) INFORMATION FOR SEQ ID NO: 28:

(i) SEQUENCE CHARACTERISTICS:

(A) LENGTH: 26
      (B) TYPE: nucleic acid
      (C) STRANDEDNESS: single
      (D) TOPOLOGY: linear (ii) SEQUENCE DESCRIPTION: SEQ ID NO: 28:

CCUGCUGUUU GACAACCAGA GCCUGC 26

(2) INFORMATION FOR SEQ ID NO: 29:

(i) SEQUENCE CHARACTERISTICS:

(A) LENGTH: 15
      (B) TYPE: nucleic acid
      (C) STRANDEDNESS: single
      (D) TOPOLOGY: linear (ii) SEQUENCE DESCRIPTION: SEQ ID NO: 29:

AAGCGCAAGA GUCCC 15

(2) INFORMATION FOR SEQ ID NO: 30:

(i) SEQUENCE CHARACTERISTICS:

(A) LENGTH: 17
      (B) TYPE: nucleic acid
      (C) STRANDEDNESS: single
      (D) TOPOLOGY: linear (ii) SEQUENCE DESCRIPTION: SEQ ID NO: 30:

GCCCCCCUCC CCGCGCC 17

(2) INFORMATION FOR SEQ ID NO: 31:

(i) SEQUENCE CHARACTERISTICS:

(A) LENGTH: 12
      (B) TYPE: nucleic acid
      (C) STRANDEDNESS: single
      (D) TOPOLOGY: linear (ii) SEQUENCE DESCRIPTION: SEQ ID NO: 31:

```
CCUCCACGCC CC                                                            12

(2) INFORMATION FOR SEQ ID NO:    32:

(i) SEQUENCE CHARACTERISTICS:

(A) LENGTH:          19
         (B) TYPE:            nucleic acid
         (C) STRANDEDNESS:    single
         (D) TOPOLOGY:        linear (ii) SEQUENCE DESCRIPTION: SEQ ID NO: 32:

GCGCCCCGUG GCCGUGUCG                                                     19

(2) INFORMATION FOR SEQ ID NO:    33:

(i) SEQUENCE CHARACTERISTICS:

(A) LENGTH:          22
         (B) TYPE:            nucleic acid
         (C) STRANDEDNESS:    single
         (D) TOPOLOGY:        linear (ii) SEQUENCE DESCRIPTION: SEQ ID NO: 33:

CCUGGAGGCC UACUGCUCCC CG                                                 22

(2) INFORMATION FOR SEQ ID NO:    34:

(i) SEQUENCE CHARACTERISTICS:

(A) LENGTH:          22
         (B) TYPE:            nucleic acid
         (C) STRANDEDNESS:    single
         (D) TOPOLOGY:        linear (ii) SEQUENCE DESCRIPTION: SEQ ID NO: 34:

CUGUUCCCCG UCCCCUGGCG AC                                                 22

(2) INFORMATION FOR SEQ ID NO:    35:

(i) SEQUENCE CHARACTERISTICS:

(A) LENGTH:          13
         (B) TYPE:            nucleic acid
         (C) STRANDEDNESS:    single
         (D) TOPOLOGY:        linear (ii) SEQUENCE DESCRIPTION: SEQ ID NO: 35:

UCAUGUUUGA CCC                                                           13

(2) INFORMATION FOR SEQ ID NO:    36:

(i) SEQUENCE CHARACTERISTICS:

(A) LENGTH:          26
         (B) TYPE:            nucleic acid
```

```
         (C) STRANDEDNESS:          single
         (D) TOPOLOGY:              linear (ii) SEQUENCE DESCRIPTION: SEQ ID NO: 36:

UGGCCUCGAU CGCCGCGCGG UGCGCC                                           26

(2) INFORMATION FOR SEQ ID NO:   37:

(i) SEQUENCE CHARACTERISTICS:

(A) LENGTH:               23
         (B) TYPE:                 nucleic acid
         (C) STRANDEDNESS:         single
         (D) TOPOLOGY:             linear (ii) SEQUENCE DESCRIPTION: SEQ ID NO: 37:

GACGACGACG AUAACCCCCA CCC                                              23

(2) INFORMATION FOR SEQ ID NO:   38:

(i) SEQUENCE CHARACTERISTICS:

(A) LENGTH:               24
         (B) TYPE:                 nucleic acid
         (C) STRANDEDNESS:         single
         (D) TOPOLOGY:             linear (ii) SEQUENCE DESCRIPTION: SEQ ID NO: 38:

AUCCCCGACC CCGAGGACGU GCGC                                             24

(2) INFORMATION FOR SEQ ID NO:   39:

(i) SEQUENCE CHARACTERISTICS:

(A) LENGTH:               12
         (B) TYPE:                 nucleic acid
         (C) STRANDEDNESS:         single
         (D) TOPOLOGY:             linear (ii) SEQUENCE DESCRIPTION: SEQ ID NO: 39:

CCCGACGUGU CG                                                          12

(2) INFORMATION FOR SEQ ID NO:   40:

(i) SEQUENCE CHARACTERISTICS:

(A) LENGTH:               26
         (B) TYPE:                 nucleic acid
         (C) STRANDEDNESS:         single
         (D) TOPOLOGY:             linear (ii) SEQUENCE DESCRIPTION: SEQ ID NO: 40:

GUGCUGGCGG CGGCGGGGGC CGUGGA                                           26

(2) INFORMATION FOR SEQ ID NO:   41:
```

(i) SEQUENCE CHARACTERISTICS:

(A) LENGTH:            18
            (B) TYPE:              nucleic acid
            (C) STRANDEDNESS:      single
            (D) TOPOLOGY:          linear (ii) SEQUENCE DESCRIPTION: SEQ ID NO: 41:

GGAGGCGGGC UUGGCCAC                                                      18

(2) INFORMATION FOR SEQ ID NO:   42:

(i) SEQUENCE CHARACTERISTICS:

(A) LENGTH:            13
            (B) TYPE:              nucleic acid
            (C) STRANDEDNESS:      single
            (D) TOPOLOGY:          linear (ii) SEQUENCE DESCRIPTION: SEQ ID NO: 42:

CUGGGACGAA GAC                                                           13

(2) INFORMATION FOR SEQ ID NO:   43:

(i) SEQUENCE CHARACTERISTICS:

(A) LENGTH:            14
            (B) TYPE:              nucleic acid
            (C) STRANDEDNESS:      single
            (D) TOPOLOGY:          linear (ii) SEQUENCE DESCRIPTION: SEQ ID NO: 43:

GGGUGCUGUA ACGG                                                          14

(2) INFORMATION FOR SEQ ID NO:   44:

(i) SEQUENCE CHARACTERISTICS:

(A) LENGTH:            24
            (B) TYPE:              nucleic acid
            (C) STRANDEDNESS:      single
            (D) TOPOLOGY:          linear (ii) SEQUENCE DESCRIPTION: SEQ ID NO: 44:

GUGAACCUUU ACCCAGCCGU CCUC                                               24

(2) INFORMATION FOR SEQ ID NO:   45:

(i) SEQUENCE CHARACTERISTICS:

(A) LENGTH:            16
            (B) TYPE:              nucleic acid
            (C) STRANDEDNESS:      single
            (D) TOPOLOGY:          linear (ii) SEQUENCE DESCRIPTION: SEQ ID NO: 45:

GCACAGCGCU UCCGUG                                                        16

(2) INFORMATION FOR SEQ ID NO:   46:

(i) SEQUENCE CHARACTERISTICS:

(A) LENGTH:              23
              (B) TYPE:                nucleic acid
              (C) STRANDEDNESS:        single
              (D) TOPOLOGY:            linear (ii) SEQUENCE DESCRIPTION: SEQ ID NO: 46:

AGCGCCAGCU AGACGGACAG AAA                                                      23

(2) INFORMATION FOR SEQ ID NO:    47:

(i) SEQUENCE CHARACTERISTICS:

(A) LENGTH:              18
              (B) TYPE:                nucleic acid
              (C) STRANDEDNESS:        single
              (D) TOPOLOGY:            linear (ii) SEQUENCE DESCRIPTION: SEQ ID NO: 47:

CACCUUCAGC AACCCGGG                                                            18

(2) INFORMATION FOR SEQ ID NO:    48:

(i) SEQUENCE CHARACTERISTICS:

(A) LENGTH:              13
              (B) TYPE:                nucleic acid
              (C) STRANDEDNESS:        single
              (D) TOPOLOGY:            linear (ii) SEQUENCE DESCRIPTION: SEQ ID NO: 48:

UAAGCGCAUC CGA                                                                 13

(2) INFORMATION FOR SEQ ID NO:    49:

(i) SEQUENCE CHARACTERISTICS:

(A) LENGTH:              11
              (B) TYPE:                nucleic acid
              (C) STRANDEDNESS:        single
              (D) TOPOLOGY:            linear (ii) SEQUENCE DESCRIPTION: SEQ ID NO: 49:

CUCGCAACAA C                                                                   11

(2) INFORMATION FOR SEQ ID NO:    50:

(i) SEQUENCE CHARACTERISTICS:

(A) LENGTH:              28
              (B) TYPE:                nucleic acid
              (C) STRANDEDNESS:        single
              (D) TOPOLOGY:            linear (ii) SEQUENCE DESCRIPTION: SEQ ID NO: 50:

CGCAAGUGCC CCAUCUGCAG UGGUUCCG                                                 28

(2) INFORMATION FOR SEQ ID NO: 51:

(i) SEQUENCE CHARACTERISTICS:

(A) LENGTH:          20
        (B) TYPE:            nucleic acid
        (C) STRANDEDNESS:    single
        (D) TOPOLOGY:        linear (ii) SEQUENCE DESCRIPTION: SEQ ID NO: 51:

GCGGCCUUAG AGUCCCCCGC                                                20

(2) INFORMATION FOR SEQ ID NO: 52:

(i) SEQUENCE CHARACTERISTICS:

(A) LENGTH:          21
        (B) TYPE:            nucleic acid
        (C) STRANDEDNESS:    single
        (D) TOPOLOGY:        linear (ii) SEQUENCE DESCRIPTION: SEQ ID NO: 52:

GGUGUAUCUU AUCACCGGCA A                                            21

(2) INFORMATION FOR SEQ ID NO: 53:

(i) SEQUENCE CHARACTERISTICS:

(A) LENGTH:          15
        (B) TYPE:            nucleic acid
        (C) STRANDEDNESS:    single
        (D) TOPOLOGY:        linear (ii) SEQUENCE DESCRIPTION: SEQ ID NO: 53:

GCUCCGGAAA GAGCA                                                        15

(2) INFORMATION FOR SEQ ID NO: 54:

(i) SEQUENCE CHARACTERISTICS:

(A) LENGTH:          23
        (B) TYPE:            nucleic acid
        (C) STRANDEDNESS:    single
        (D) TOPOLOGY:        linear (ii) SEQUENCE DESCRIPTION: SEQ ID NO: 54:

CAGACAAUCA ACGAGGUCUU GGA                                        23

(2) INFORMATION FOR SEQ ID NO: 55:

(i) SEQUENCE CHARACTERISTICS:

(A) LENGTH:          28
        (B) TYPE:            nucleic acid
        (C) STRANDEDNESS:    single
        (D) TOPOLOGY:        linear (ii) SEQUENCE DESCRIPTION: SEQ ID NO: 55:

UGGUGACGGG CGCCACGCGC AUUGCGGC                                       28

(2) INFORMATION FOR SEQ ID NO:    56:

(i) SEQUENCE CHARACTERISTICS:

(A) LENGTH:           16
        (B) TYPE:             nucleic acid
        (C) STRANDEDNESS:     single
        (D) TOPOLOGY:         linear (ii) SEQUENCE DESCRIPTION: SEQ ID NO: 56:

CCAAAACAUG UACGCC                                                    16

(2) INFORMATION FOR SEQ ID NO:    57:

(i) SEQUENCE CHARACTERISTICS:

(A) LENGTH:           22
        (B) TYPE:             nucleic acid
        (C) STRANDEDNESS:     single
        (D) TOPOLOGY:         linear (ii) SEQUENCE DESCRIPTION: SEQ ID NO: 57:

UCAACACCAU CUUUCAUGAA UU                                             22

(2) INFORMATION FOR SEQ ID NO:    58:

(i) SEQUENCE CHARACTERISTICS:

(A) LENGTH:           32
        (B) TYPE:             nucleic acid
        (C) STRANDEDNESS:     single
        (D) TOPOLOGY:         linear (ii) SEQUENCE DESCRIPTION: SEQ ID NO: 58:

CCAACUGGGA CAGUACCCGU ACACCCUGAC CA                                  32

(2) INFORMATION FOR SEQ ID NO:    59:

(i) SEQUENCE CHARACTERISTICS:

(A) LENGTH:           32
        (B) TYPE:             nucleic acid
        (C) STRANDEDNESS:     single
        (D) TOPOLOGY:         linear (ii) SEQUENCE DESCRIPTION: SEQ ID NO: 59:

ACCUGCAGCG ACGAGAUCUG ACGUACUACU GG                                  32

(2) INFORMATION FOR SEQ ID NO:    60:

(i) SEQUENCE CHARACTERISTICS:

(A) LENGTH:           19
        (B) TYPE:             nucleic acid
        (C) STRANDEDNESS:     single
        (D) TOPOLOGY:         linear (ii) SEQUENCE DESCRIPTION: SEQ ID NO: 60:

ACGAAGCGCG CCCUGGCCG                                                  19

(2) INFORMATION FOR SEQ ID NO:   61:

(i) SEQUENCE CHARACTERISTICS:

(A) LENGTH:            17
              (B) TYPE:              nucleic acid
              (C) STRANDEDNESS:      single
              (D) TOPOLOGY:          linear (ii) SEQUENCE DESCRIPTION: SEQ ID NO: 61:

CCUGACGCGG UUGGCCC                                                    17

(2) INFORMATION FOR SEQ ID NO:   62:

(i) SEQUENCE CHARACTERISTICS:

(A) LENGTH:            15
              (B) TYPE:              nucleic acid
              (C) STRANDEDNESS:      single
              (D) TOPOLOGY:          linear (ii) SEQUENCE DESCRIPTION: SEQ ID NO: 62:

CUUUACCCGC AGCAA                                                      15

(2) INFORMATION FOR SEQ ID NO:   63:

(i) SEQUENCE CHARACTERISTICS:

(A) LENGTH:            14
              (B) TYPE:              nucleic acid
              (C) STRANDEDNESS:      single
              (D) TOPOLOGY:          linear (ii) SEQUENCE DESCRIPTION: SEQ ID NO: 63:

UCGUCAUCGA CGAG                                                       14

(2) INFORMATION FOR SEQ ID NO:   64:

(i) SEQUENCE CHARACTERISTICS:

(A) LENGTH:            25
              (B) TYPE:              nucleic acid
              (C) STRANDEDNESS:      single
              (D) TOPOLOGY:          linear (ii) SEQUENCE DESCRIPTION: SEQ ID NO: 64:

GCCGGGCUCC UUGGGCGUCA CCUCC                                           25

(2) INFORMATION FOR SEQ ID NO:   65:

(i) SEQUENCE CHARACTERISTICS:

(A) LENGTH:            13

```
            (B) TYPE:                  nucleic acid
            (C) STRANDEDNESS:          single
            (D) TOPOLOGY:              linear (ii) SEQUENCE DESCRIPTION: SEQ ID NO: 65:

GCCGUGGUGU AUU                                                              13

(2) INFORMATION FOR SEQ ID NO:    66:

(i) SEQUENCE CHARACTERISTICS:

(A) LENGTH:                16
            (B) TYPE:                  nucleic acid
            (C) STRANDEDNESS:          single
            (D) TOPOLOGY:              linear (ii) SEQUENCE DESCRIPTION: SEQ ID NO: 66:

CGGCCCGCCU GCGGCC                                                           16

(2) INFORMATION FOR SEQ ID NO:    67:

(i) SEQUENCE CHARACTERISTICS:

(A) LENGTH:                16
            (B) TYPE:                  nucleic acid
            (C) STRANDEDNESS:          single
            (D) TOPOLOGY:              linear (ii) SEQUENCE DESCRIPTION: SEQ ID NO: 67:

CCUGGAGUCG ACCUUC                                                           16

(2) INFORMATION FOR SEQ ID NO:    68:

(i) SEQUENCE CHARACTERISTICS:

(A) LENGTH:                11
            (B) TYPE:                  nucleic acid
            (C) STRANDEDNESS:          single
            (D) TOPOLOGY:              linear (ii) SEQUENCE DESCRIPTION: SEQ ID NO: 68:

CGUCCGCCAG A                                                                11

(2) INFORMATION FOR SEQ ID NO:    69:

(i) SEQUENCE CHARACTERISTICS:

(A) LENGTH:                32
            (B) TYPE:                  nucleic acid
            (C) STRANDEDNESS:          single
            (D) TOPOLOGY:              linear (ii) SEQUENCE DESCRIPTION: SEQ ID NO: 69:

UCAUCUGCAA CCGCACGCUG CGCGAGUACG CC                                         32

(2) INFORMATION FOR SEQ ID NO:    70:

(i) SEQUENCE CHARACTERISTICS:
```

(A) LENGTH:           22
        (B) TYPE:             nucleic acid
        (C) STRANDEDNESS:     single
        (D) TOPOLOGY:         linear (ii) SEQUENCE DESCRIPTION: SEQ ID NO: 70:

CGCCUCUCGU AUAGCUGGGC CA                                        22

(2) INFORMATION FOR SEQ ID NO:  71:

(i) SEQUENCE CHARACTERISTICS:

(A) LENGTH:           18
        (B) TYPE:             nucleic acid
        (C) STRANDEDNESS:     single
        (D) TOPOLOGY:         linear (ii) SEQUENCE DESCRIPTION: SEQ ID NO: 71:

UUUUUAUUAA CAACAAAC                                             18

(2) INFORMATION FOR SEQ ID NO:  72:

(i) SEQUENCE CHARACTERISTICS:

(A) LENGTH:           27
        (B) TYPE:             nucleic acid
        (C) STRANDEDNESS:     single
        (D) TOPOLOGY:         linear (ii) SEQUENCE DESCRIPTION: SEQ ID NO: 72:

ACCUCAUGAA GGUGCUGGAG UACGGCC                                   27

(2) INFORMATION FOR SEQ ID NO:  73:

(i) SEQUENCE CHARACTERISTICS:

(A) LENGTH:           28
        (B) TYPE:             nucleic acid
        (C) STRANDEDNESS:     single
        (D) TOPOLOGY:         linear (ii) SEQUENCE DESCRIPTION: SEQ ID NO: 73:

GGCCUGCCCA UCACCGAGGA GCACAUGC                                  28

(2) INFORMATION FOR SEQ ID NO:  74:

(i) SEQUENCE CHARACTERISTICS:

(A) LENGTH:           22
        (B) TYPE:             nucleic acid
        (C) STRANDEDNESS:     single
        (D) TOPOLOGY:         linear (ii) SEQUENCE DESCRIPTION: SEQ ID NO: 74:

CCGGAAAACU ACAUCACCAA CC                                        22

(2) INFORMATION FOR SEQ ID NO:  75:

(i) SEQUENCE CHARACTERISTICS:

(A) LENGTH:          21
    (B) TYPE:            nucleic acid
    (C) STRANDEDNESS:    single
    (D) TOPOLOGY:        linear (ii) SEQUENCE DESCRIPTION: SEQ ID NO: 75:

CCGCCAACCU CCCCGGCUGG A                                    21

(2) INFORMATION FOR SEQ ID NO: 76:

(i) SEQUENCE CHARACTERISTICS:

(A) LENGTH:          30
        (B) TYPE:            nucleic acid
        (C) STRANDEDNESS:    single
        (D) TOPOLOGY:        linear (ii) SEQUENCE DESCRIPTION: SEQ ID NO: 76:

UGUUCUCCUC CCACAAAGAG GUGAGCGCGU                         30

(2) INFORMATION FOR SEQ ID NO: 77:

(i) SEQUENCE CHARACTERISTICS:

(A) LENGTH:          11
        (B) TYPE:            nucleic acid
        (C) STRANDEDNESS:    single
        (D) TOPOLOGY:        linear (ii) SEQUENCE DESCRIPTION: SEQ ID NO: 77:

ACCCGUGAGG G                                                11

(2) INFORMATION FOR SEQ ID NO: 78:

(i) SEQUENCE CHARACTERISTICS:

(A) LENGTH:          11
        (B) TYPE:            nucleic acid
        (C) STRANDEDNESS:    single
        (D) TOPOLOGY:        linear (ii) SEQUENCE DESCRIPTION: SEQ ID NO: 78:

CUUACGUUCG U                                                  11

(2) INFORMATION FOR SEQ ID NO: 79:

(i) SEQUENCE CHARACTERISTICS:

(A) LENGTH:          17
        (B) TYPE:            nucleic acid
        (C) STRANDEDNESS:    single
        (D) TOPOLOGY:        linear (ii) SEQUENCE DESCRIPTION: SEQ ID NO: 79:

CAAGGAGUUU GACGAAU                                        17

(2) INFORMATION FOR SEQ ID NO: 80:

(i) SEQUENCE CHARACTERISTICS:
    (A) LENGTH: 18
    (B) TYPE: nucleic acid
    (C) STRANDEDNESS: single
    (D) TOPOLOGY: linear (ii) SEQUENCE DESCRIPTION: SEQ ID NO: 80:

CGGCCUGACG AUUGAAAA      18

(2) INFORMATION FOR SEQ ID NO: 81:

(i) SEQUENCE CHARACTERISTICS:
    (A) LENGTH: 25
    (B) TYPE: nucleic acid
    (C) STRANDEDNESS: single
    (D) TOPOLOGY: linear (ii) SEQUENCE DESCRIPTION: SEQ ID NO: 81:

AUCACCAACU ACUCGCAGAG CCAGG      25

(2) INFORMATION FOR SEQ ID NO: 82:

(i) SEQUENCE CHARACTERISTICS:
    (A) LENGTH: 17
    (B) TYPE: nucleic acid
    (C) STRANDEDNESS: single
    (D) TOPOLOGY: linear (ii) SEQUENCE DESCRIPTION: SEQ ID NO: 82:

GAGGUGCACA GCAAACA      17

(2) INFORMATION FOR SEQ ID NO: 83:

(i) SEQUENCE CHARACTERISTICS:
    (A) LENGTH: 17
    (B) TYPE: nucleic acid
    (C) STRANDEDNESS: single
    (D) TOPOLOGY: linear (ii) SEQUENCE DESCRIPTION: SEQ ID NO: 83:

UGGUCGUGGC CCGCAAC      17

(2) INFORMATION FOR SEQ ID NO: 84:

(i) SEQUENCE CHARACTERISTICS:
    (A) LENGTH: 26
    (B) TYPE: nucleic acid
    (C) STRANDEDNESS: single
    (D) TOPOLOGY: linear (ii) SEQUENCE DESCRIPTION: SEQ ID NO: 84:

CUCAACAGCC AGAUCGCGGU GACCGC      26

(2) INFORMATION FOR SEQ ID NO: 85:

(i) SEQUENCE CHARACTERISTICS:

(A) LENGTH: 22
        (B) TYPE: nucleic acid
        (C) STRANDEDNESS: single
        (D) TOPOLOGY: linear (ii) SEQUENCE DESCRIPTION: SEQ ID NO: 85:

GCGCCUGCGA AAACUGGUUU UU                    22

(2) INFORMATION FOR SEQ ID NO: 86:

(i) SEQUENCE CHARACTERISTICS:

(A) LENGTH: 15
        (B) TYPE: nucleic acid
        (C) STRANDEDNESS: single
        (D) TOPOLOGY: linear (ii) SEQUENCE DESCRIPTION: SEQ ID NO: 86:

GCUUUGUAAA GACUC                          15

(2) INFORMATION FOR SEQ ID NO: 87:

(i) SEQUENCE CHARACTERISTICS:

(A) LENGTH: 20
        (B) TYPE: nucleic acid
        (C) STRANDEDNESS: single
        (D) TOPOLOGY: linear (ii) SEQUENCE DESCRIPTION: SEQ ID NO: 87:

ACAACUUUCU GCAGCGCCCG                    20

(2) INFORMATION FOR SEQ ID NO: 88:

(i) SEQUENCE CHARACTERISTICS:

(A) LENGTH: 11
        (B) TYPE: nucleic acid
        (C) STRANDEDNESS: single
        (D) TOPOLOGY: linear (ii) SEQUENCE DESCRIPTION: SEQ ID NO: 88:

UGCGACCCAG A                              11

(2) INFORMATION FOR SEQ ID NO: 89:

(i) SEQUENCE CHARACTERISTICS:

(A) LENGTH: 30
        (B) TYPE: nucleic acid
        (C) STRANDEDNESS: single
        (D) TOPOLOGY: linear (ii) SEQUENCE DESCRIPTION: SEQ ID NO: 89:

UCGCCUACGC CCGCAUGGGA GAACUAACGG                                    30

(2) INFORMATION FOR SEQ ID NO:    90:

(i) SEQUENCE CHARACTERISTICS:

(A) LENGTH:            15
        (B) TYPE:              nucleic acid
        (C) STRANDEDNESS:      single
        (D) TOPOLOGY:          linear (ii) SEQUENCE DESCRIPTION: SEQ ID NO: 90:

UUGAUUUUAA GCAAC                                                   15

(2) INFORMATION FOR SEQ ID NO:    91:

(i) SEQUENCE CHARACTERISTICS:

(A) LENGTH:            11
        (B) TYPE:              nucleic acid
        (C) STRANDEDNESS:      single
        (D) TOPOLOGY:          linear (ii) SEQUENCE DESCRIPTION: SEQ ID NO: 91:

CCCGGACGAU U                                                       11

(2) INFORMATION FOR SEQ ID NO:    92:

(i) SEQUENCE CHARACTERISTICS:

(A) LENGTH:            9
        (B) TYPE:              nucleic acid
        (C) STRANDEDNESS:      single
        (D) TOPOLOGY:          linear (ii) SEQUENCE DESCRIPTION: SEQ ID NO: 92:

UGGACGAAC                                                          9

(2) INFORMATION FOR SEQ ID NO:    93:

(i) SEQUENCE CHARACTERISTICS:

(A) LENGTH:            32
        (B) TYPE:              nucleic acid
        (C) STRANDEDNESS:      single
        (D) TOPOLOGY:          linear (ii) SEQUENCE DESCRIPTION: SEQ ID NO: 93:

AACAGCUCGA CGUGUUUUAC UGCCACUACA CC                                32

(2) INFORMATION FOR SEQ ID NO:    94:

(i) SEQUENCE CHARACTERISTICS:

(A) LENGTH:            24
        (B) TYPE:              nucleic acid
        (C) STRANDEDNESS:      single
        (D) TOPOLOGY:          linear (ii) SEQUENCE DESCRIPTION: SEQ ID NO: 94:

```
CCGCCGUUCA CACCCAGUUU GCGC                                          24

(2) INFORMATION FOR SEQ ID NO:  95:

(i) SEQUENCE CHARACTERISTICS:

(A) LENGTH:             26
        (B) TYPE:               nucleic acid
        (C) STRANDEDNESS:       single
        (D) TOPOLOGY:           linear (ii) SEQUENCE DESCRIPTION:  SEQ ID NO: 95:

CGGGCCUUCC UCGGGAGAUU CCGAAU                                        26

(2) INFORMATION FOR SEQ ID NO:  96:

(i) SEQUENCE CHARACTERISTICS:

(A) LENGTH:             13
        (B) TYPE:               nucleic acid
        (C) STRANDEDNESS:       single
        (D) TOPOLOGY:           linear (ii) SEQUENCE DESCRIPTION:  SEQ ID NO: 96:

AAGAGCUCUU CGG                                                      13

(2) INFORMATION FOR SEQ ID NO:  97:

(i) SEQUENCE CHARACTERISTICS:

(A) LENGTH:             16
        (B) TYPE:               nucleic acid
        (C) STRANDEDNESS:       single
        (D) TOPOLOGY:           linear (ii) SEQUENCE DESCRIPTION:  SEQ ID NO: 97:

CAUUUGAAGU CGCCCC                                                   16

(2) INFORMATION FOR SEQ ID NO:  98:

(i) SEQUENCE CHARACTERISTICS:

(A) LENGTH:             30
        (B) TYPE:               nucleic acid
        (C) STRANDEDNESS:       single
        (D) TOPOLOGY:           linear (ii) SEQUENCE DESCRIPTION:  SEQ ID NO: 98:

CGUACGUGGA CAACGUUAUC UUCCGGGGCU                                    30

(2) INFORMATION FOR SEQ ID NO:  99:

(i) SEQUENCE CHARACTERISTICS:

(A) LENGTH:             11
        (B) TYPE:               nucleic acid
        (C) STRANDEDNESS:       single
        (D) TOPOLOGY:           linear
```

(ii) SEQUENCE DESCRIPTION: SEQ ID NO: 99:

AUGCUGACCG G                                                                                11

(2) INFORMATION FOR SEQ ID NO:    100:

(i) SEQUENCE CHARACTERISTICS:
                (A) LENGTH:             23
                (B) TYPE:               nucleic acid
                (C) STRANDEDNESS:       single
                (D) TOPOLOGY:           linear (ii) SEQUENCE DESCRIPTION: SEQ ID NO: 100:

CGCGCGGGGG GCUGAUGUCC GUC                                                                   23

(2) INFORMATION FOR SEQ ID NO:    101:

(i) SEQUENCE CHARACTERISTICS:
                (A) LENGTH:             22
                (B) TYPE:               nucleic acid
                (C) STRANDEDNESS:       single
                (D) TOPOLOGY:           linear (ii) SEQUENCE DESCRIPTION: SEQ ID NO: 101:

AGACGGACAA UUAUACGCUC AU                                                                    22

(2) INFORMATION FOR SEQ ID NO:    102:

(i) SEQUENCE CHARACTERISTICS:
                (A) LENGTH:             13
                (B) TYPE:               nucleic acid
                (C) STRANDEDNESS:       single
                (D) TOPOLOGY:           linear (ii) SEQUENCE DESCRIPTION: SEQ ID NO: 102:

CGCACGGGUG UUU                                                                              13

(2) INFORMATION FOR SEQ ID NO:    103:

(i) SEQUENCE CHARACTERISTICS:
                (A) LENGTH:             27
                (B) TYPE:               nucleic acid
                (C) STRANDEDNESS:       single
                (D) TOPOLOGY:           linear (ii) SEQUENCE DESCRIPTION: SEQ ID NO: 103:

CCAACGUGGC CGAGUUACUG GAAGAGG                                                               27

(2) INFORMATION FOR SEQ ID NO:    104:

(i) SEQUENCE CHARACTERISTICS:
                (A) LENGTH:             11
                (B) TYPE:               nucleic acid
                (C) STRANDEDNESS:       single
                (D) TOPOLOGY:           linear (ii) SEQUENCE DESCRIPTION: SEQ ID NO: 104:

CCCCCCUGCC U                                                                11

(2) INFORMATION FOR SEQ ID NO: 105:

(i) SEQUENCE CHARACTERISTICS:
        (A) LENGTH:         26
        (B) TYPE:           nucleic acid
        (C) STRANDEDNESS:   single
        (D) TOPOLOGY:       linear (ii) SEQUENCE DESCRIPTION: SEQ ID NO: 105:

CACGGCUUCA UGUCCGUCGU CAACAC                                                26

(2) INFORMATION FOR SEQ ID NO: 106:

(i) SEQUENCE CHARACTERISTICS:
        (A) LENGTH:         15
        (B) TYPE:           nucleic acid
        (C) STRANDEDNESS:   single
        (D) TOPOLOGY:       linear (ii) SEQUENCE DESCRIPTION: SEQ ID NO: 106:

CAACACCCAA CAUCA                                                            15

(2) INFORMATION FOR SEQ ID NO: 107:

(i) SEQUENCE CHARACTERISTICS:
        (A) LENGTH:         29
        (B) TYPE:           nucleic acid
        (C) STRANDEDNESS:   single
        (D) TOPOLOGY:       linear (ii) SEQUENCE DESCRIPTION: SEQ ID NO: 107:

GCCAUGGCCA UAAACGCCGA CUACGGCAU                                             29

(2) INFORMATION FOR SEQ ID NO: 108:

(i) SEQUENCE CHARACTERISTICS:
        (A) LENGTH:         26
        (B) TYPE:           nucleic acid
        (C) STRANDEDNESS:   single
        (D) TOPOLOGY:       linear (ii) SEQUENCE DESCRIPTION: SEQ ID NO: 108:

ACAAGGUCGC CAUCUGCUUU ACGCCC                                                26

(2) INFORMATION FOR SEQ ID NO: 109:

(i) SEQUENCE CHARACTERISTICS:
        (A) LENGTH:         18
        (B) TYPE:           nucleic acid
        (C) STRANDEDNESS:   single
        (D) TOPOLOGY:       linear (ii) SEQUENCE DESCRIPTION: SEQ ID NO: 109:

GGCAACCUGC GCCUCAAC                                                     18

(2) INFORMATION FOR SEQ ID NO:   110:

(i) SEQUENCE CHARACTERISTICS:
            (A) LENGTH:           22
            (B) TYPE:             nucleic acid
            (C) STRANDEDNESS:     single
            (D) TOPOLOGY:         linear (ii) SEQUENCE DESCRIPTION: SEQ ID NO: 110:

CCUCCUCCGA AUUCCUUCGC AU                                                22

(2) INFORMATION FOR SEQ ID NO:   111:

(i) SEQUENCE CHARACTERISTICS:
            (A) LENGTH:           12
            (B) TYPE:             nucleic acid
            (C) STRANDEDNESS:     single
            (D) TOPOLOGY:         linear (ii) SEQUENCE DESCRIPTION: SEQ ID NO: 111:

CGAUGACGUC AU                                                           12

(2) INFORMATION FOR SEQ ID NO:   112:

(i) SEQUENCE CHARACTERISTICS:
            (A) LENGTH:           31
            (B) TYPE:             nucleic acid
            (C) STRANDEDNESS:     single
            (D) TOPOLOGY:         linear (ii) SEQUENCE DESCRIPTION: SEQ ID NO: 112:

UCGGCUCUGC GCGAUCCGAA CGUGGUCAUU G                                      31

(2) INFORMATION FOR SEQ ID NO:   113:

(i) SEQUENCE CHARACTERISTICS:
            (A) LENGTH:           24
            (B) TYPE:             nucleic acid
            (C) STRANDEDNESS:     single
            (D) TOPOLOGY:         linear (ii) SEQUENCE DESCRIPTION: SEQ ID NO: 113:

UCUAUUAACC CGCCGUCCCC UUAC                                              24

(2) INFORMATION FOR SEQ ID NO:   114:

(i) SEQUENCE CHARACTERISTICS:
            (A) LENGTH:           19
            (B) TYPE:             nucleic acid
            (C) STRANDEDNESS:     single
            (D) TOPOLOGY:         linear -continued (ii) SEQUENCE DESCRIPTION: SEQ ID NO: 114:

GGGGGACUCA CUACCCACC                        19

(2) INFORMATION FOR SEQ ID NO:   115:

(i) SEQUENCE CHARACTERISTICS:
        (A) LENGTH:          23
        (B) TYPE:            nucleic acid
        (C) STRANDEDNESS:    single
        (D) TOPOLOGY:        linear (ii) SEQUENCE DESCRIPTION: SEQ ID NO: 115:

GCGAGAUGUC CAAUCCACAG ACG                   23

METHOD AND REAGENT FOR INHIBITING HERPES SIMPLEX VIRUS REPLICATION

This is a continuation of U.S. Ser. No. 08/623,891, filed on Mar. 25, 1996 now U.S. Pat. No. 5,795,778; which is a continuation of U.S. Ser. No. 08/238,200, filed on May 4, 1994, now abandoned; which is a continuation of U.S. Ser. No. 07/987,133, filed on Dec. 7, 1992, now abandoned; which is a continuation-in-part of U.S. Ser. No. 07/948,359, filed on Sep. 18, 1992, now abandoned; which is a continuation-in-part of U.S. Ser. No. 07/882,921, filed May 14, 1992, now abandoned.

BACKGROUND OF THE INVENTION

This invention relates to reagents useful as inhibitors of herpes simplex virus (HSV) replication and gene expression.

The following is a discussion of relevant art, none of which is admitted to be prior art to the pending claims.

Human herpes viruses cause a wide variety of diseases which result in significant levels of morbidity and mortality worldwide. The HSV group accounts for about one million new cases of infection each year in the United States. These infections are maintained for the lifetime of the patient as latent viral infections, which can be stimulated to reactivate by a variety of factors. The manifestations of HSV infection range from mild infections of herpes labialis to more serious infections such as herpes encephalitis.

HSV contains a double-stranded DNA genome within its central core, has a molecular weight of approximately 100 million, and a genome encoding at least 70 polypeptides. The DNA core is surrounded by a capsid constructed from capsomers arranged in icosapentahedral symmetry. Tightly adherent to the capsid is the tegument, which appears to consist of amorphous material. Loosely surrounding the capsid and tegument is a lipid bilayer envelope containing polyamines, lipids, and the viral glycoproteins. These glycoproteins confer distinctive properties to the virus and provide unique antigens to which the host is capable of responding. Glycoprotein G (gG), for example, confers antigenic specificity to HSV, and therefore results in an antibody response that can be used to distinguish HSV-1 (gG-1) from HSV-2 (gG-2).

Replication of HSV is a multi-step process. Following the onset of infection, DNA is uncoated and transported to the nucleus of the host cell. Transcription of immediate-early genes encoding various regulatory proteins follows. Expression of immediate-early gene products is then followed by the expression of proteins encoded by early and then late genes, including structural proteins as well as proteins necessary for viral replication. Assembly of the viral core and capsid takes place within the nucleus. This is followed by envelopment at the nuclear membrane and transport out of the nucleus through the endoplasmic reticulum and the Golgi apparatus, where viral envelope proteins are glycosylated. Mature virons are transported to the outer membrane of the host cell, and release of progeny virus is accompanied by cell death. Replication for all herpesviruses is considered inefficient, with a high ratio of noninfectious to infectious viral particles.

The complete sequence of the HSV-1 genome is known. McGeoch et al., 69 *J. Gen. Virol.* 1531, 1988; McGeoch et al., 14 *Nucleic Acid Res.* 1727, 1986; and the elucidation of the HSV-2 genome sequence is underway in laboratories worldwide. The two subtypes of HSV, HSV-1 and HSV-2, are 60–80% homologous at the DNA level, but intragenic variation, where known, is less.

Antiviral drugs including acyclovir have been used to effectively treat HSV infections, although with limited success. For example, chronic treatment with acyclovir has resulted in the development of acyclovir-resistant strains. Nucleoside analogs, such as acycloguanosine and trifluorothymidine are currently used for treatment of mucosal and ocular HSV infections, but these compounds have little if any effect upon recurrent or secondary infections (which are becoming more prevalent as the number of HIV-immunosuppressed patients rises). In addition, nucleoside analogs are poorly soluble in aqueous solutions, are rapidly catabolized intracellularly, and can be extremely toxic.

SUMMARY OF THE INVENTION

The invention features novel enzymatic RNA molecules, or ribozymes, and methods for their use for inhibiting HSV replication. Such ribozymes can be used in a method for treatment of diseases caused by these viruses in man and other animals, including other primates.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Natl. Acad. of Sci.* USA 8788, 1987, Haseloff and Gerlach, 334 *Nature* 585, 1988, Cech, 260 *JAMA* 3030, 1988, and Jefferies et al., 17 *Nucleic Acid Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

These ribozymes exhibit a high degree of specificity for only the virally encoded mRNA in infected cells. Ribozyme molecules targeted to highly conserved sequence regions will allow the treatment of many species or subtypes of HSV with a single compound. There is no acceptable treatment which will give a broad spectrum of activity with no toxic side effects. No treatment exists which specifically attacks viral gene expression which is responsible for the transformation of epithelial cells by HSV, for the maintenance of the episomal genome in latently infected cells or for the vegetative replication of the virus in permissive cells.

The methods of this invention can be used to treat HSV infections, which includes these diseases noted above. The utility can be extended to other HSV-like virus which infect non-human primates where such infections are of veterinary importance.

Thus, in the first aspect the invention features an enzymatic RNA molecule (or ribozyme) which specifically cleaves HSV expressed RNA. The ribozymes of the invention are capable of specifically cleaving particular viral mRNA targets, resulting in the destruction of mRNA transcript integrity required for translation, and therefore preventing the synthesis of the encoded protein. More specifically, the ribozymes of the invention are targeted to and prevent the translation of mRNAs encoding proteins required for viral genomic replication, virion structure, and viral infectivity, maintenance of the latent state, etc., and therefore interfere with critical events required for viral survival. Thus, diseases caused by HSV may be effectively treated by ribozyme-mediated interruption of the viral life-cycle.

Preferred cleavage sites are at genes required for viral replication, e.g., protein synthesis, such as in the immediate early genes (ICP0, ICP4, ICP22 and ICP27), genes required for nucleic acid metabolism (UL13, 39, 40, 50), host shut-off (UL41), control of late viral protein synthesis (γ 34.5), DNA replication (UL5, 8, 9, 29, 30, 42, 53) and structural protein encoding genes (gB and gC).

Alternative regions make suitable targets of ribozyme-mediated inhibition of HSV replication. Most preferred targets include ICP4(IE3), ICP27(UL54), UL39, UL40, UL5, γ 34.5 and UL27(gB) genes. Below are provided examples of ribozymes targeted to the ICP4 gene but other such ribozymes are expected to have utility at these other genes.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. 100% complementarity is preferred, but complementarity as low as 50–75% may also be useful in this invention. By "equivalent" RNA to HSV is meant to include those naturally occurring viral encoded RNA molecules associated with viral caused diseases in various animals, including humans, and other primates. These viral encoded RNAs have similar structures and equivalent genes to each other.

In preferred embodiments, the enzymatic RNA molecule is formed in a hammerhead motif, but may also be formed in the motif of a hairpin, hepatitis delta virus, group I intron or RNAseP RNA (in association with an RNA guide sequence). Examples of such hammerhead motifs are described by Rossi et al., 8 *Aids Research and Human Retroviruses* 183, 1992, of hairpin motifs by Hampel et al., "RNA Catalyst for Cleaving Specific RNA Sequences", filed Sep. 20, 1989, which is a continuation-in-part of U.S. Ser. No. 07/247,100 filed Sep. 20, 1988, Hampel and Tritz, 28 *Biochemistry* 4929, 1989 and Hampel et al., 18 *Nucleic Acids Research* 299, 1990, and an example of the hepatitis delta virus motif is described by Perrotta and Been, 31 *Biochemistry* 16, 1992, of the RNAseP motif by Guerrier-Takada et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In particularly preferred embodiments, the RNA which is cleaved is HSV ICP4 or UL5 mRNA regions (for UL5, nucleotide #1 is defined by preliminary mapping of the cap site in our laboratory and nucleotide 2800 is the site of translation initiation for the UL4 protein whose open reading frame is also included in the UL5 mRNA) selected from one or more of the following sequences:

TABLE I

| ICP4 nucleotide number | sequence | |
|---|---|---|
| 52 | AGAGACAGACCGUCAGACGCUC | (SEQ. ID. NO. 1) |
| 81 | CCGGGACGCCGAUAC | (SEQ. ID. NO. 2) |
| 116 | GGAUCGGCCGUCCCUGUCCU | (SEQ. ID. NO. 3) |
| 143 | ACCCAAGCAUCGACCGGUCC | (SEQ. ID. NO. 4) |
| 212 | GGUCUCGCCCCUCCCCCC | (SEQ. ID. NO. 5) |
| 236 | UAGGUGACCUACCGUGCUACGUCCGCCGUCG | (SEQ. ID. NO. 6) |
| 273 | UAUCCCCGGAGGA | (SEQ. ID. NO. 7) |
| 304 | GGCGUCGGAGAACAAGCAGCGCCCCGGCUCC | (SEQ. ID. NO. 8) |
| 458 | CACGACCUCGAC | (SEQ. ID. NO. 9) |
| 532 | CGCCGUCUCGCCGCGACAGCUGGCUCUGCUG | (SEQ. ID. NO. 10) |

TABLE I-continued

| | | |
|---|---|---|
| 584 | GUCCGGACGAUCCCGACGCCC | (SEQ. ID. NO. 11) |
| 647 | GACGACGAUGACGGGACGAGUACGACGACG | (SEQ. ID. NO. 12) |
| 745 | GUAUCCGGACCCCAC | (SEQ. ID. NO. 13) |
| 803 | CGUCGUCACGGCC | (SEQ. ID. NO. 14) |
| 834 | CAUAGACCT | (SEQ. ID. NO. 15) |
| 871 | GUCCGCAUCCUCU | (SEQ. ID. NO. 16) |
| 1092 | GCAUCGAGCGCC | (SEQ. ID. NO. 17) |
| 1140 | GGGCCGCUUCACGGCCGGGCAG | (SEQ. ID. NO. 18) |
| 1345 | GCGACGCCGGUUCGAGGC | (SEQ. ID. NO. 19) |
| 1419 | ACGCCCUGAUCACG | (SEQ. ID. NO. 20) |
| 1465 | GGGGUGGCUCCAGAACC | (SEQ. ID. NO. 21) |
| 1547 | AACAGCAGCUCCUUCAUCACCGGCAGCGUGG | (SEQ. ID. NO. 22) |
| 1632 | GCCUGGCGCACGC | (SEQ. ID. NO. 23) |
| 1652 | CCGUGGCCAUGA | (SEQ. ID. NO. 24) |
| 1672 | AUACGACCGCGC | (SEQ. ID. NO. 25) |
| 1682 | GCGCAGAAGGGCUUCCUGCUGAC | (SEQ. ID. NO. 26) |
| 2012 | GCCUGCCGCGGGAUCCUGGAGGCGCUGG | (SEQ. ID. NO. 27) |
| 2368 | CCUGCUGUUUGACAACCAGAGCCUGC | (SEQ. ID. NO. 28) |
| 2483 | AAGCGCAAGAGUCCC | (SEQ. ID. NO. 29) |
| 2585 | GCCCCCUCCCCGCGCC | (SEQ. ID. NO. 30) |
| 2610 | CCUCCACGCCCC | (SEQ. ID. NO. 31) |
| 2686 | GCGCCCCGUGGCCGUGUCG | (SEQ. ID. NO. 32) |
| 2794 | CCUGGAGGCCACUGCUCCCCG | (SEQ. ID. NO. 33) |
| 2846 | CUGUUCCCCGUCCCCUGGCGAC | (SEQ. ID. NO. 34) |
| 2874 | UCAUGUUUGACCC | (SEQ. ID. NO. 35) |
| 2895 | UGGCCUCGAUCGCCGCGCGGUGCGCC | (SEQ. ID. NO. 36) |
| 2960 | GACGACGACGAUAACCCCCACCC | (SEQ. ID. NO. 37) |
| 3165 | AUCCCCGACCCCGAGGACGUGCGC | (SEQ. ID. NO. 38) |
| 3243 | CCCGACGUGUCG | (SEQ. ID. NO. 39) |
| 4038 | GUGCUGGCGGCGGCGGGGGCCGUGGA | (SEQ. ID. NO. 40) |
| 4076 | GGAGGCGGGCUUGGCCAC | (SEQ. ID. NO. 41) |
| 4130 | CUGGGACGAAGAC | (SEQ. ID. NO. 42) |
| 4168 | GGGUGCUGUAACGG | (SEQ. ID. NO. 43) |

| UL5 nucleotide number | sequence | |
|---|---|---|
| 1 | GUGAACCUUUACCCAGCCGUCCUC | (SEQ. ID. NO. 44) |
| 30 | GCACAGCGCUUCCGUG | (SEQ. ID. NO. 45) |
| 110 | AGCGCCAGCUAGACGGACAGAAA | (SEQ. ID. NO. 46) |
| 145 | CACCUUCAGCAACCCGGG | (SEQ. ID. NO. 47) |

TABLE I-continued

| | | |
|---|---|---|
| 237 | UAAGCGCAUCCGA | (SEQ. ID. NO. 48) |
| 255 | CUCGCAACAAC | (SEQ. ID. NO. 49) |
| 278 | CGCAAGUGCCCCAUCUGCAGUGGUUCCG | (SEQ. ID. NO. 50) |
| 313 | GCGGCCUUAGAGUCCCCCGC | (SEQ. ID. NO. 51) |
| 363 | GGUGUAUCUUAUCACCGGCAA | (SEQ. ID. NO. 52) |
| 389 | GCUCCGGAAAGAGCA | (SEQ. ID. NO. 53) |
| 412 | CAGACAAUCAACGAGGUCUUGGA | (SEQ. ID. NO. 54) |
| 440 | UGGUGACGGGCGCCACGCGCAUUGCGGC | (SEQ. ID. NO. 55) |
| 468 | CCAAAACAUGUACGCC | (SEQ. ID. NO. 56) |
| 515 | UCAACACCAUCUUUCAUGAAUU | (SEQ. ID. NO. 57) |
| 564 | CCAACUGGGACAGUACCCGUACACCCUGACCA | (SEQ. ID. NO. 58) |
| 617 | ACCUGCAGCGACGAGAUCUGACGUACUACUGG | (SEQ. ID. NO. 59) |
| 667 | ACGAAGCGCGCCCUGGCCG | (SEQ. ID. NO. 60) |
| 765 | CCUGACGCGGUUGGCCC | (SEQ. ID. NO. 61) |
| 807 | CUUUACCCGCAGCAA | (SEQ. ID. NO. 62) |
| 827 | UCGUCAUCGACGAG | (SEQ. ID. NO. 63) |
| 841 | GCCGGGCUCCUUGGGCGUCACCUCC | (SEQ. ID. NO. 64) |
| 871 | GCCGUGGUGUAUU | (SEQ. ID. NO. 65) |
| 926 | CGGCCCGCCUGCGGCC | (SEQ. ID. NO. 66) |
| 981 | CCUGGAGUCGACCUUC | (SEQ. ID. NO. 67) |
| 1020 | CGUCCGCCAGA | (SEQ. ID. NO. 68) |
| 1052 | UCAUCUGCAACCGCACGCUGCGCGAGUACGCC | (SEQ. ID. NO. 69) |
| 1084 | CGCCUCUCGUAUAGCUGGGCCA | (SEQ. ID. NO. 70) |
| 1106 | UUUUUAUUAACAACAAAC | (SEQ. ID. NO. 71) |
| 1148 | ACCUCAUGAAGGUGCUGGAGUACGGCC | (SEQ. ID. NO. 72) |
| 1170 | GGCCUGCCCAUCACCGAGGAGCACAUGC | (SEQ. ID. NO. 73) |
| 1212 | CCGGAAAACUACAUCACCAACC | (SEQ. ID. NO. 74) |
| 1234 | CCGCCAACCUCCCCGGCUGGA | (SEQ. ID. NO. 75) |
| 1271 | UGUUCUCCUCCACAAAGAGGUGAGCGCGU | (SEQ. ID. NO. 76) |
| 1333 | ACCCGUGAGGG | (SEQ. ID. NO. 77) |
| 1372 | CUUACGUUCGU | (SEQ. ID. NO. 78) |
| 1389 | CAAGGAGUUUGACGAAU | (SEQ. ID. NO. 79) |
| 1428 | CGGCCUGACGAUUGAAAA | (SEQ. ID. NO. 80) |
| 1471 | AUCACCAACUACUCGCAGAGCCAGG | (SEQ. ID. NO. 81) |
| 1522 | GAGGUGCACAGCAAACA | (SEQ. ID. NO. 82) |
| 1544 | UGGUCGUGGCCCGCAAC | (SEQ. ID. NO. 83) |
| 1576 | CUCAACAGCCAGAUCGCGGUGACCGC | (SEQ. ID. NO. 84) |
| 1602 | GCGCCUGCGAAAACUGGUUUUU | (SEQ. ID. NO. 85) |
| 1673 | GCUUUGUAAAGACUC | (SEQ. ID. NO. 86) |
| 1760 | ACAACUUUCUGCAGCGCCCG | (SEQ. ID. NO. 87) |

TABLE I-continued

| | | |
|---|---|---|
| 1788 | UGCGACCCAGA | (SEQ. ID. NO. 88) |
| 1805 | UCGCCUACGCCCGCAUGGGAGAACUAACGG | (SEQ. ID. NO. 89) |
| 1915 | UUGAUUUUAAGCAAC | (SEQ. ID. NO. 90) |
| 1959 | CCCGGACGAUU | (SEQ. ID. NO. 91) |
| 2006 | UGGACGAAC | (SEQ. ID. NO. 92) |
| 2014 | AACAGCUCGACGUGUUUUACUGCCACUACACC | (SEQ. ID. NO. 93) |
| 2068 | CCGCCGUUCACACCCAGUUUGCGC | (SEQ. ID. NO. 94) |
| 2301 | CGGGCCUUCCUCGGGAGAUUCCGAAU | (SEQ. ID. NO. 95) |
| 2132 | AAGAGCUCUUCGG | (SEQ. ID. NO. 96) |
| 2150 | CAUUUGAAGUCGCCCC | (SEQ. ID. NO. 97) |
| 2174 | CGUACGUGGACAACGUUAUCUUCCGGGGCU | (SEQ. ID. NO. 98) |
| 2209 | AUGCUGACCGG | (SEQ. ID. NO. 99) |
| 2225 | CGCGCGGGGGCUGAUGUCCGUC | (SEQ. ID. NO.100) |
| 2255 | AGACGGACAAUUAUACGCUCAU | (SEQ. ID. NO.101) |
| 2289 | CGCACGGGUGUUU | (SEQ. ID. NO.102) |
| 2339 | CCAACGUGGCCGAGUUACUGGAAGAGG | (SEQ. ID. NO.103) |
| 2366 | CCCCCCUGCCU | (SEQ. ID. NO.104) |
| 2398 | CACGGCUUCAUGUCCGUCGUCAACAC | (SEQ. ID. NO.105) |
| 2418 | CAACACCCAACAUCA | (SEQ. ID. NO.106) |
| 2467 | GCCAUGGCCAUAAACGCCGACUACGGCAU | (SEQ. ID. NO.107) |
| 2546 | ACAAGGUCGCCAUCUGCUUUACGCCC | (SEQ. ID. NO.108) |
| 2572 | GGCAACCUGCGCCUCAAC | (SEQ. ID. NO.109) |
| 2618 | CCUCCUCCGAAUUCCUUCGCAU | (SEQ. ID. NO.110) |
| 2673 | CGAUGACGUCAU | (SEQ. ID. NO.111) |
| 2701 | UCGGCUCUGCGCGAUCCGAACGUGGUCAUUG | (SEQ. ID. NO.112) |
| 2732 | UCUAUUAACCCGCCGUCCCCUUAC | (SEQ. ID. NO.113) |
| 2776 | GGGGGACUCACUACCCACC | (SEQ. ID. NO.114) |
| 2795 | GCGAGAUGUCCAAUCCACAGACG | (SEQ. ID. NO.115) |

In a second related aspect, the invention features a mammalian cell which includes an enzymatic RNA molecule as described above. Preferably, the mammalian cell is a human or other primate cell.

In a third related aspect, the invention features an expression vector which includes nucleic acid encoding the enzymatic RNA molecules described above, located in the vector, e.g., in a manner which allows expression of that enzymatic RNA molecule within a mammalian cell.

In a fourth related aspect, the invention features a method for treatment of a HSV-caused disease by administering to a patient an enzymatic RNA molecule which cleaves HSV-encoded RNA or related RNA in the regions discussed above.

The invention provides a class of chemical cleaving agents which exhibit a high degree of specificity for the viral RNA of HSV-infected cells. The ribozyme molecule is preferably targeted to a highly conserved sequence region of an HSV such that all types and strains of this virus can be treated with a single ribozyme. Such enzymatic RNA molecules can be delivered exogenously to infected cells. In the preferred hammerhead motif the small size (less than 40 nucleotides, preferably between 32 and 36 nucleotides in length) of the molecule allows the cost of treatment to be reduced compared to other ribozyme motifs.

Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, small ribozyme motifs (e.g., of the hammerhead structure, shown generally in FIG. 1) are used for exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure or with complementary binding of the ribozyme to the mRNA target region.

The enzymatic RNA molecules of this invention can be used to treat HSV infections. Infected animals can be treated at the time of productive infection. This timing of treatment will reduce viral loads in infected cells and disable viral replication in any subsequent rounds of infection. This is possible because the preferred ribozymes disable those structures required for successful initiation of viral protein synthesis. For treatment of transformed cervical epithelia or keratinocytes, the method of this invention will inhibit the expression of viral genes known to cause cell immortalization. For treatment of latent viral infections, this invention will inhibit gene expression required for the maintenance of the viral episomal genome.

The preferred targets of the present invention are advantageous over other targets since they act not only during the productive infection but also in latently infected cells and in virally transformed cells. In addition, viral particles which are released during a first round of infection in the presence of such ribozymes will still be immunogenic by virtue of having their capsids intact. Thus, one method of this invention allows the creation of defective but immunogenic viral particles, and thus a continued possibility of initiation of an immune response in a treated animal.

In addition, the enzymatic RNA molecules of this invention can be used in vitro in a cell culture transfected with HSV DNA to produce defective viral particles. These particles can then be used for instigation of immune responses in a prophylactic manner, or as a treatment of infected animals.

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). (See, Thompson and Draper, "Method and Reagent for Treatment of Neuroblastoma"; Draper, "Method and Reagent for Treatment of a Stenotic Condition; Sullivan and Draper, "Method and Reagent for Treatment of Inflammatory Disease"; and Draper, "Method and Reagent for Treatment of Arthritic Conditions"; all filed on the same date as the present application, and all hereby incorporated by reference herein.)

Other features and advantages of the invention will be apparent from the following description of the preferred embodiments thereof, and from the claims.

DESCRIPTION OF THE PREFERRED EMBODIMENTS

Figure 1:
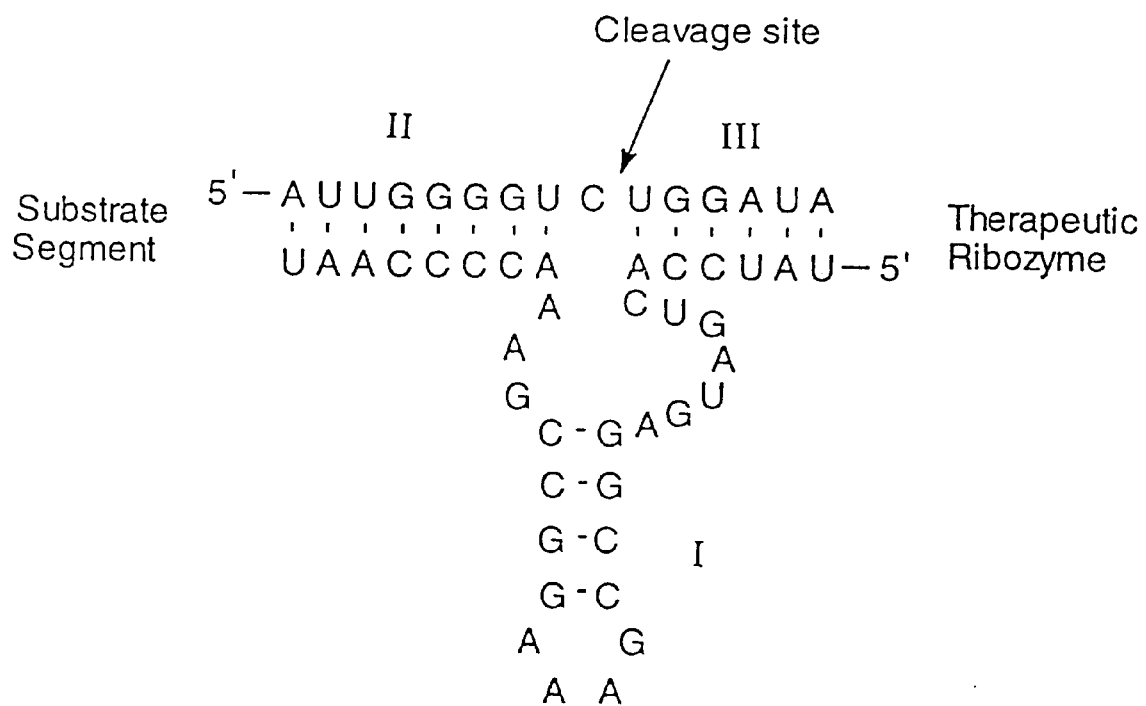

The drawing will first briefly be described.

DRAWING

FIG. 1 is a diagrammatic representation of a hammerhead motif ribozyme showing stems I, II and III (marked (I), (II) and (III) respectively) interacting with a target region. The 5' and 3' ends of both ribozyme and target are shown. Dashes indicate base-paired nucleotides.

Target Sites

Those regions (genes) of the genome which are essential for HSV replication are expected to maintain a constant sequence (i.e., are conserved) over extensive periods of time. These regions are preferred target sites in this invention since they are more likely to be conserved between different types or strains of HSV, and thus only one ribozyme is needed to destroy all viral RNA. Thus, one ribozyme may be used to target all HSV-encoded RNA. We have selected several such genes of these viruses, and analyzed the structure of the encoded mRNAs using RNA-fold computer analyses. We have identified open structures in the RNAs which may be cleaved by ribozymes targeted to those regions. Two regions analyzed in detail are the HSV-1 ICP4 and UL5 mRNAs; other genes can be analyzed in a manner similar to that described below.

Ribozymes targeting selected regions of the HSV mRNA are preferably chosen to cleave the target RNA in a manner which inhibits translation of the RNA. Genes are selected such that such viral replication is inhibited, e.g., by inhibiting protein synthesis. Selection of effective ribozymes to cleave target sites within these critical regions of viral mRNA entails testing the accessibility of the target mRNA to hybridization with various oligonucleotide probes. These studies can be performed using RNA probes and assaying accessibility by cleaving the hybrid molecule with RNAseH (see below). Alternatively, such a study can use ribozyme probes designed from secondary structure predictions of the RNAs, and assaying cleavage products by polyacrylamide gel electrophoresis (PAGE), to detect the presence of cleaved and uncleaved molecules.

HSV specific ribozymes may be designed to also inhibit other herpesviruses, particularly varicella zoster virus (VZV), which exhibits significant intragenic nucleotide homology with a number of analogous HSV genes. For example, the VZV immediate-early protein IE62 exhibits considerable amino acid homology to the HSV immediate-early regulatory protein ICP4/IE3 and is a major component of VZV particles (Kinchington et al., 66 *J. Virol.* 359, 1992). Also, some transcription units and their encoded proteins are conserved within the genomes of evolutionarily divergent human herpesviruses, and ribozyme targets within these genetic units may therefore provide the basis for designing ribozymes with broad therapeutic applications.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

The mRNA sequences of the viruses are analyzed throughout the regions discussed above (using the nucleotide sequence of the HSV-1 ICP4 gene (EMBL No.

HEHSV1G3, nucleotides 1176–5435) and UL5 gene). Putative ribozyme cleavage sites are found to be weak or non-base paired regions of the virus mRNA. These sites represent the preferred sites for hammerhead or other ribozyme cleavage within these target RNAs.

Short RNA substrates corresponding to each of the gene sites are designed. Each substrate is composed of two to three nucleotides at the 5' and 3' ends that will not base pair with a corresponding ribozyme recognition region. The unpaired regions flank a central region of 12–14 nucleotides to which complementary arms in the ribozyme are designed.

The structure of each substrate sequence is predicted using a PC fold computer program. Sequences which give a positive free energy of binding are accepted. Sequences which give a negative free energy are modified by trimming one or two bases from each of the ends. If the modified sequences are still predicted to have a strong secondary structure, they are rejected.

After substrates are chosen, ribozymes are designed to each of the RNA substrates. Ribozyme folding is also analyzed using PC fold.

Ribozyme molecules are sought which form hammerhead motif stem II (see FIG. 1) regions and contain flanking arms which are devoid of intramolecular base pairing. Often the ribozymes are modified by trimming a base from the ends of the ribozyme, or by introducing additional base pairs in stem II to achieve the desired fold. Ribozymes with incorrect folding are rejected. After substrate/ribozyme pairs are found to contain correct intramolecular structures, the molecules are folded together to predict intermolecular interactions. A schematic representation of a ribozyme with its coordinate base pairing to its cognate target sequence is shown in FIG. 1.

Using such analyses, predictions of effective target sites in the viral mRNAs, based upon computer generated structural analyses, were obtained (see SEQ ID NOS. 1–115). The target region is listed with the nucleotide number (in the HSV-1 ICP4 or UL5 mRNA) noted as base number.

Those targets thought to be useful as ribozyme targets can be tested to determine accessibility to nucleic acid probes in a ribonuclease H assay (see below). This assay provides a quick test of the use of the target site without requiring synthesis of a ribozyme. It can be used to screen for sites most suited for ribozyme attack.

Synthesis of Ribozymes

Ribozymes useful in this invention can be produced by gene transcription as described by Cech, supra, or by chemical synthesis. Chemical synthesis of RNA is similar to that for DNA synthesis. The additional 2'-OH group in RNA, however, requires a different protecting group strategy to deal with selective 3'–5' internucleotide bond formation, and with RNA susceptibility to degradation in the presence of bases. The recently developed method of RNA synthesis utilizing the t-butyldimethylsilyl group for the protection of the 2' hydroxyl is the most reliable method for synthesis of ribozymes. The method reproducibly yields RNA with the correct 3'–5' internucleotide linkages, with average coupling yields in excess of 99%, and requires only a two-step deprotection of the polymer.

A method based on H-phosphonate chemistry exhibits a relatively lower coupling efficiency than a method based upon the phosphoramidite chemistry. This is a problem for synthesis of DNA as well. A promising approach to scale-up of automatic oligonucleotide synthesis has been described recently for the H-phosphonates. A combination of a proper coupling time and additional capping of "failure" sequences gave high yields in the synthesis of oligodeoxynucleotides in scales in the range of 14 micromoles with as little as 2 equivalents of a monomer in the coupling step. Another alternative approach is to use soluble polymeric supports (e.g., polyethylene glycols), instead of the conventional solid supports. This method can yield short oligonucleotides in hundred milligram quantities per batch utilizing about 3 equivalents of a monomer in a coupling step.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Exogenous delivery of ribozymes benefits from chemical modification of the backbone, e.g., by the overall negative charge of the ribozyme molecule being reduced to facilitate diffusion across the cell membrane. The present strategies for reducing the oligonucleotide charge include: modification of internucleotide linkages by ethylphosphonates, use of phosphoramidites, linking oligonucleotides to positively charged molecules, and creating complex packages composed of oligonucleotides, lipids and specific receptors or effectors for targeted cells. Examples of such modifications include sulfur-containing ribozymes containing phosphorothioates and phosphorodithioates as internucleotide linkages in RNA. Synthesis of such sulfur-modified ribozymes is achieved by use of the sulfur-transfer reagent, $^3$H-1,2-benzenedithiol-3-one 1,1-dioxide. Ribozymes may also contain ribose modified ribonucleotides. Pyrimidine analogues are prepared from uridine using a procedure employing diethylamino sulphur trifluoride (DAST) as a starting reagent. Ribozymes can also be either electrostatically or covalently attached to polymeric cations for the purpose of reducing charge. The polymer can be attached to the ribozyme by simply converting the 3'-end to a ribonucleoside dialdehyde which is obtained by a periodate cleavage of the terminal 2',3'-cis diol system. Depending on the specific requirements for delivery systems, other possible modifications may include different linker arms containing carboxyl, amino or thiol functionalities. Yet further examples include use of methylphosphonates and 2'-O-methylribose and 5' or 3' capping or blocking with $m_7$GpppG or $m_3^{2,2,7}$GpppG.

For example, a kinased ribozyme is contacted with guanosine triphosphate and guanyltransferase to add a $m^3G$ cap to the ribozyme. After such synthesis, the ribozyme can be gel purified using standard procedure. To ensure that the ribozyme has the desired activity, it may be tested with and without the 5' cap using standard procedures to assay both its enzymatic activity and its stability.

Synthetic ribozymes, including those containing various modifiers, can be purified by high pressure liquid chromatography (HPLC). Other liquid chromatography techniques, employing reverse phase columns and anion exchangers on silica and polymeric supports may also be used.

There follows an example of the synthesis of one ribozyme. A solid phase phosphoramidite chemistry is employed. Monomers used are 2'-tert-butyl-dimethylsilyl cyanoethylphosphoramidities of uridine, N-benzoyl-cytosine, N-phenoxyacetyl adenosine and guanosine (Glen Research, Sterling, Va.). Solid phase synthesis is carried out on either an ABI 394 or 380B DNA/RNA synthesizer using the standard protocol provided with each machine. The only exception is that the coupling step is increased from 10 to 12 minutes. The phosphoramidite concentration is 0.1 M. Synthesis is done on a 1 µmole scale using a 1 µmole RNA reaction column (Glen Research). The average coupling efficiencies are between 97% and 98% for the 394 model, and between 97% and 99% for the 380B model, as determined by a calorimetric measurement of the released trityl cation.

Blocked ribozymes are cleaved from the solid support (e.g., CPG), and the bases and diphosphoester moiety deprotected in a sterile vial by dry ethanolic ammonia (2 mL) at 55° C. for 16 hours. The reaction mixture is cooled on dry ice. Later, the cold liquid is transferred into a sterile screw cap vial and lyophilized.

To remove the 2'-tert-butyl-dimethylsilyl groups from the ribozyme, the residue is suspended in 1 M tetra-n-butylammonium fluoride in dry THF (TBAF), using a 20 fold excess of the reagent for every silyl group, for 16 hours at ambient temperature (about 15–25° C.). The reaction is quenched by adding an equal volume of sterile 1 M triethylamine acetate, pH 6.5. The sample is cooled and concentrated on a SpeedVac to half the initial volume.

The ribozymes are purified in two steps by HPLC on a C4 300 Å 5 mm DeltaPak column in an acetonitrile gradient.

The first step, or "trityl on" step, is a separation of 5'-DMT-protected ribozyme(s) from failure sequences lacking a 5'-DMT group. Solvents used for this step are: A (0.1 M triethylammonium acetate, pH 6.8) and B (acetonitrile). The elution profile is: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step is a purification of a completely deblocked ribozyme by a treatment of 2% trifluoroacetic acid on a C4 300 Å 5 mm DeltaPak column in an acetonitrile gradient. Solvents used for this second step are: A (0.1 M Triethylammonium acetate, pH 6.8) and B (80% acetonitrile, 0.1 M triethylammonium acetate, pH 6.8). The elution profile is: 5% B for 5 minutes, a linear gradient of 5% B to 15% B over 60 minutes, 15% B for 10 minutes, and a linear gradient of 15% B to 0% B over 10 minutes.

The fraction containing ribozyme is cooled and lyophilized on a SpeedVac. Solid residue is dissolved in a minimum amount of ethanol and sodium perchlorate in acetone. The ribozyme is collected by centrifugation, washed three times with acetone, and lyophilized.

Expression Vector

While synthetic ribozymes are preferred in this invention, those produced by expression vectors can also be used. In designing a suitable ribozyme expression vector the following factors are important to consider. The final ribozyme must be kept as small as possible to minimize unwanted secondary structure within the ribozyme. A promoter (e.g., the human cytomegalovirus immediate early region promoter or keratin promoters from human keratin genes) should be chosen to be a relatively strong promoter, and expressible both in vitro and in vivo. Such a promoter should express the ribozyme at a level suitable to effect production of enough ribozyme to destroy a target RNA, but not at too high a level to prevent other cellular activities from occurring (unless cell death itself is desired).

A hairpin at the 5' end of the ribozyme is useful to ensure that the required transcription initiation sequence (GG or GGG or GGGAG) does not bind to some other part of the ribozyme and thus affect regulation of the transcription process. The 5' hairpin is also useful to protect the ribozyme from 5'–3' exonucleases. A selected hairpin at the 3' end of the ribozyme is useful since it acts as both a transcription termination signal, and as a protection from 3'–5' exonucleases. One example of a known termination signal is that present on the T7 RNA polymerase system. This signal is about 30 nucleotides in length. Other 3' hairpins of shorter length can be used to provide good termination and RNA stability. Such hairpins can be inserted within the vector sequences to allow standard ribozymes to be placed in an appropriate orientation and expressed with such sequences attached.

Poly(A) tails are also useful to protect the 3' end of the ribozyme. These can be provided by either including a poly(A) signal site in the expression vector (to signal a cell to add the poly(A) tail in vivo), or by introducing a poly(A) sequence directly into the expression vector. In the first approach the signal must be located to prevent unwanted secondary structure formation with other parts of the ribozyme. In the second approach, the poly(A) stretch may reduce in size over time when expressed in vivo, and thus the vector may need to be checked over time. Care must be taken in addition of a poly(A) tail which binds poly(A) binding proteins which prevent the ribozyme from acting.

Ribozyme Testing

Once the desired ribozymes are selected, synthesized and purified, they are tested in kinetic and other experiments to determine their utility. An example of such a procedure is provided below.

Preparation of Ribozyme

Crude synthetic ribozyme (typically 350 $\mu$g at a time) is purified by separation on a 15% denaturing polyacrylamide gel (0.75 mm thick, 40 cm long) and visualized by UV shadowing. Once excised, gel slices containing full length ribozyme are soaked in 5 ml gel elution buffer (0.5 M $NH_4OAc$, 1 mM EDTA) overnight with shaking at 4° C. The eluent is desalted over a C-18 matrix (Sep-Pak cartridges, Millipore, Milford, Mass.) and vacuum dried. The dried RNA is resuspended in 50–100 $\mu$l TE (TRIS 10 mM, EDTA 1 mM, pH 7.2). An aliquot of this solution is diluted 100 fold into 1 ml TE, half of which is used to spectrophotometrically quantitate the ribozyme solution. The concentration of this dilute stock is typically 150–800 nM. Purity of the ribozyme is confirmed by the presence of a single band on a denaturing polyacrylamide gel.

A ribozyme may advantageously be synthesized in two or more portions. Each portion of a ribozyme will generally have only limited or no enzymatic activity, and the activity will increase substantially (by at least 5–10 fold) when all portions are ligated (or otherwise juxtaposed) together. A specific example of hammerhead ribozyme synthesis is provided below.

The method involves synthesis of two (or more) shorter "half" ribozymes and ligation of them together using T4 RNA ligase. For example, to make a 34 mer ribozyme, two 17 mers are synthesized, one is phosphorylated, and both are gel purified. These purified 17 mers are then annealed to a DNA splint strand complementary to the two 17 mers. This DNA splint has a sequence designed to locate the two 17 mer portions with one end of each adjacent each other. The juxtaposed RNA molecules are then treated with T4 RNA ligase in the presence of ATP. The 34 mer RNA so formed is then HPLC purified.

Preparation of Substrates

Approximately 10–30 pmoles of unpurified substrate is radioactively 5' end-labelled with T4 polynucleotide kinase using 25 pmoles of [$\gamma$-$^{32}$P] ATP. The entire labelling mix is separated on a 20% denaturing polyacrylamide gel and visualized by autoradiography. The full length band is excised and soaked overnight at 4° C. in 100 μl of TE (10 mM Tris-HCl pH 7.6, 0.1 mM EDTA).

Kinetic Reactions

For reactions using short substrates (between 8 and 16 bases) a substrate solution is made 1× in assay buffer (75 mM Tris-HCl, pH 7.6; 0.1 mM EDTA, 10 mM MgCl$_2$) such that the concentration of substrate is less than 1 nM. A ribozyme solution (typically 20 nM) is made 1× in assay buffer and four dilutions are made using 1× assay buffer. Fifteen μl of each ribozyme dilution (i.e., 20, 16, 12, 8 and 4 nM) is placed in a separate tube. These tubes and the substrate tube are pre-incubated at 37° C. for at least five minutes.

The reaction is started by mixing 15 μl of substrate into each ribozyme tube by rapid pipetting (note that final ribozyme concentrations are 10, 8, 6, 4, 2 nM). 5 μl aliquots are removed at 15 or 30 second intervals and quenched with 5 μl stop solution (95% formamide, 20 mM EDTA xylene cyanol, and bromphenol blue dyes). Following the final ribozyme time point, an aliquot of the remaining substrate is removed as a zero ribozyme control.

The samples are separated on either 15% or 20% polyacrylamide gels. Each gel is visualized and quantitated with an Ambis beta scanner (Ambis Systems, San Diego, Calif.).

For the most active ribozymes, kinetic analyses are performed in substrate excess to determine $K_m$ and $K_{cat}$ values.

For kinetic reactions with long RNA substrates (greater than 15 bases in length) the substrates are prepared by transcription using T7 RNA polymerase and defined templates containing a T7 promoter, and DNA encoding appropriate nucleotides of the viral RNA. The substrate solution is made 1× in assay buffer (75 mM Tris-HCl, pH 7.6; 0.1 mM EDTA; 10 mM MgCl$_2$) and contains 58 nanomolar concentration of the long RNA molecules. The reaction is started by addition of gel purified ribozymes to 1 μM concentration. Aliquots are removed at 20, 40, 60, 80 and 100 minutes, then quenched by the addition of 5 μl stop solution. Cleavage products are separated using denaturing PAGE. The bands are visualized and quantitated with an Ambis beta scanner. In one example, a long substrate RNA transcript corresponding to nucleotides 1–493 of the HSV-1 ICP4 mRNA is synthesized in vitro with T7 RNA polymerase from a defined template containing T7 promoter and DNA encoding nucleotides 1–493 of ICP4.

EXAMPLE 1

Cleavage of Short Substrate RNAs Corresponding to ICP4 Gene Targets

Substrate/ribozyme pairs were evaluated for predicted structural characteristics as described above. Nine candidate substrate/ribozyme pairs were tested for their capacity to cleave substrate RNAs in vitro in a ribozyme cleavage assay described above. Of these nine ribozymes, seven were targeted to the 5' end of the ICP4 mRNA and two ribozymes were targeted to the 3' end of the mRNA. Values for the $k_{cat}$, $k_m$ and $k_{cat}/k_m$ (the "cleavage constant") were experimentally determined for each of these ribozymes based upon the assay reactions. The results are presented in Table II. The $k_{cat}/k_m$ values for several of these ribozymes are higher than those recently observed for HIV-specific ribozymes in our laboratory. Ribozyme G was extremely active in this assay, with a calculated $k_{cat}/k_m$ of approximately $1 \times 10^8$ M$^{-1}$ min$^{-1}$, the highest level of activity observed using this assay. The generally high level of activity observed suggests that factors other than correct folding and the GUC cleavage region influence the structural characteristics of ribozyme-substrate interaction.

TABLE II

RIBOZYME CLEAVAGE OF SHORT ICP4 TARGET RNA SUBSTRATES

| Ribozyme | ICP4 Cleavage Site[1] | | $k_{cat}/k_m$ | $k_{cat}$ | $k_m$ |
|---|---|---|---|---|---|
| A | 66 | (1) | $2 \times 10^7$ M$^{-1}$ min$^{-1}$ | | |
| B | 177 | | no activity | | |
| C | 200 | | $6 \times 10^7$ M$^{-1}$ min$^{-1}$ | 1.73 min$^{-1}$ | 34 nM |
| D | 231 | | no activity | | |
| E | 309 | (8) | $5.3 \times 10^7$ M$^{-1}$ min$^{-1}$ | | |
| F | 864,888 | | $3.4 \times 10^6$ M$^{-1}$ min$^{-1}$ | | |
| G | 870,894 | | $1.17 \times 10^8$ M$^{-1}$ min$^{-1}$ | 5.7 min$^{-1}$ | 127 nM |
| H | 3271 | | no activity | | |
| I | 3559 | | $5 \times 10^7$ | 2.2 min$^{-1}$ | 69 nM |

[1]Nucleotide number relative to EMBL HSV-1 ICP4 gene sequence. Numbers in parentheses correspond to target SEQ ID NOS.

EXAMPLE 2

Cleavage of Long Substrate RNA's Corresponding to ICP4 Gene

The ability of three ribozymes to catalyze the cleavage of an approximately 490 nucleotide long ICP4 RNA substrate (corresponding to nucleotides 1–493 of ICP4 and prepared as described above was determined using the ribozyme cleavage assay described above. The assays were preformed in ribozyme excess and approximate $k_{cat}/k_m$ values were calculated. The results are presented in Table III. The cleavage constants for short substrate cleavage by each ribozyme are also included for comparison.

The results indicate that, generally, ribozyme cleavage of long substrates proceeds at a slower rate compared to cleavage activities on short substrates, although cleavage activity is not altogether eliminated by the use of the longer substrate. The effect of using a longer substrate varied among the five ribozymes tested, indicating that the accessibility and structural parameters of different cleavage sites change unpredictably when presented in the context of the longer RNA substrates.

All three of the ribozymes exhibited a low capacity to catalyze the long substrate relative to their activities on the shorter substrates. Two of the ribozymes, ribozymes A and E, were relatively more effective at catalyzing cleavage of the longer substrate RNA.

These results demonstrate that structural characteristics of the substrate RNA may influence ribozyme catalytic activity.

TABLE III

EFFECT OF SUBSTRATE RNA SIZE ON RIBOZYME ACTIVITY

| Ribozyme | Substrate Length[1] | $K_{cat}/k_m$ (M$^{-1}$ min$^{-1}$) | % Activity on Short Substrate |
|---|---|---|---|
| A | 17 | $2 \times 10^7$ | 100 |
|   | 490 | $4 \times 10^4$ | 57 |
| C | 17 | $6 \times 10^7$ | 100 |
|   | 490 | $5 \times 10^2$ | 8 |
| E | 17 | $5.3 \times 10^7$ | 100 |
|   | 490 | $2 \times 10^3$ | 17 |

[1]In nucleotides.

Kinetic Analysis

A simple reaction mechanism for ribozyme-mediated cleavage is:

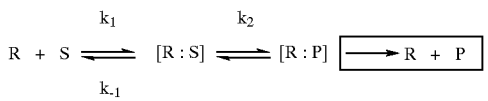

where R=ribozyme, S=substrate, and P=products. The boxed step is important only in substrate excess. Because ribozyme concentration is in excess over substrate concentration, the concentration of the ribozyme-substrate complex ([R:S]) is constant over time except during the very brief time when the complex is being initially formed, i.e.,:

$$\frac{d[R:S]}{dt} = 0$$

where t=time, and thus:

$$(R)(S)k_1 = (RS)(k_2 + k_1).$$

The rate of the reaction is the rate of disappearance of substrate with time:

$$\text{Rate} = \frac{-d(S)}{dt} = k_2(RS)$$

Substituting these expressions:

$$(R)(S)k_1 = 1/k_2 \frac{-d(S)}{dt}(k_2 + k_1)$$

or:

$$\frac{-d(S)}{S} = \frac{k_1 k_2}{(k_2 + k_1)}(R)\, dt$$

Integrating this expression with respect to time yields:

$$-\ln\frac{S}{S_0} = \frac{k_1 k_2}{(k_2 + k_1)}(R)t$$

where $S_0$=initial substrate. Therefore, a plot of the negative log of fraction substrate uncut versus time (in minutes) yields a straight line with slope:

$$\text{slope} = \frac{k_1 k_2}{(k_2 + k_1)}(R) = k_{obs}$$

where $k_{obs}$=observed rate constant. A plot of slope ($k_{obs}$) versus ribozyme concentration yields a straight line with a slope which is:

$$\text{slope} = \frac{k_1 k_2}{(k_2 + k_1)} \text{ which is } \frac{k_{cat}}{K_m}$$

Using these equations the data obtained from the kinetic experiments provides the necessary information to determine which ribozyme tested is most useful, or active. Such ribozymes can be selected and tested in in vivo or ex vivo systems.

Liposome Preparation

There follows an example of the entrapment of ribozyme molecules within a liposome drug delivery vehicle. Lipid molecules were dissolved in a volatile organic solvent ($CHCl_3$, methanol, diethylether, ethanol, etc.). The organic solvent was removed by evaporation. The lipid was hydrated into suspension with 0.1× phosphate buffered saline (PBS), then freeze-thawed 3× using liquid nitrogen and incubation at room temperature. The suspension was extruded sequentially through a 0.4 μm, 0.2 μm and 0.1 μm polycarbonate filters at maximum pressure of 800 psi. The ribozyme was mixed with the extruded liposome suspension and lyophilized to dryness. The lipid/ribozyme powder was rehydrated with water to one-tenth the original volume. The suspension was diluted to the minimum volume required for extrusion (0.4 ml for 1.5 ml barrel and 1.5 ml for 10 ml barrel) with 1×PBS and re-extruded through 0.4 μm, 0.2 μm, 0.1 μm polycarbonate filters. The liposome entrapped ribozyme was separated from untrapped ribozyme by gel filtration chromatography (SEPHAROSE CL-4B, BIOGEL A5M). The liposome extractions were pooled and sterilized by filtration through a 0.2 μm filter. The free ribozyme was pooled and recovered by ethanol precipitation. The liposome concentration was determined by incorporation of a radioactive lipid. The ribozyme concentration was determined by labeling with $^{32}P$. Rossi et al., 1992, supra (and references cited therein), describe other methods suitable for preparation of liposomes.

In experiments with a liposome formulation composed of a synthetic lipid derivative disteraoylphosphatidylethylamidothioacetyl succinimide (DSPE-ATS) coformulated with dipalmitoylphosphatidyl choline and cholesterol we observed uptake of 100 and 200 nm diameter liposomes with similar kinetics. The larger particles accommodated a larger number of entrapped molecules, or larger molecular weight molecules, such as an expression plasmid. These particles showed a linear relationship between the lipid dose offered and the mean log fluorescence (calcine was used to follow liposome uptake). No cytotoxicity was observed even with a 200 μM dose. These liposomes are particularly useful for delivery to CD4 cell populations.

In Vivo Assay

The efficacy of action of a chosen ribozyme may be tested in vivo by use of cell cultures sensitive to HSV, using standard procedures. For example, monolayer cultures of HSV-sensitive cells are grown in tissue culture plates or in raft cultures of HSV-permissive cells as described previously. Kopan et al., 105 *J. Cell Biol.* 427, 1987. Prior to transfection with HSV DNA, cultures are treated for three to 24 hours with ribozyme-containing liposomes. Cells are then rinsed with phosphate buffered saline (PBS). After transfection the cells are treated for three to five days with appropriate liposome preparations and medium changes. Viral RNA is harvested using the guanidinium isothiocyanate procedure and the resultant RNA preparation is subjected to analysis using the RNAse protection assay.

Alternatively, transformed cell types (e.g., Vero cells) are used to assess the ability of ribozyme preparations to cleave HSV mRNA and reduce the expression of target proteins. Cell monolayers are treated with ribozyme containing liposome preparations for between 3 and 96 hrs. For RNA analyses, the cells are lysed in guanidine isothiocyanate solutions and the RNA are analyzed using the RNAse protection assay. For protein quantitation, cell lysates are prepared according to methods known to those in the art and proteins are quantified by immunoanalysis using anti-HSV protein specific antibodies.

Ribonuclease Protection Assay

The accumulation of target mRNA in cells or the cleavage of the RNA by ribozymes or RNAseH (in vitro or in vivo) can be quantified using an RNAse protection assay.

In this method, antisense riboprobes are transcribed from template DNA using T7 RNA polymerase (U.S. Biochemicals) in 20 μl reactions containing 1× transcription buffer (supplied by the manufacturer), 0.2 mM ATP, GTP and UTP, 1 U/μl pancreatic RNAse inhibitor (Boehringer Mannheim Biochemicals) and 200 μCi $^{32}$P-labeled CTP (800 Ci/mmol, New England Nuclear) for 1 hour at 37° C. Template DNA is digested with 1 U RNAse-free DNAse I (U.S. Biochemicals, Cleveland, Ohio) at 37° C. for 15 minutes and unincorporated nucleotides removed by G-50 SEPHADEX spin chromatography.

In a manner similar to the transcription of antisense probe, the target RNA can be transcribed in vitro using a suitable DNA template. The transcript is purified by standard methods and digested with ribozyme at 37° C. according to methods described later.

Alternatively, virus-infected cells are harvested into 1 ml of PBS, transferred to a 1.5 ml EPPENDORF tube, pelleted for 30 seconds at low speed in a microcentrifuge, and lysed in 70 μl of hybridization buffer (4 M guanidine isothiocyanate, 0.1% sarcosyl, 25 mM sodium citrate, pH 7.5). Cell lysate (45 μl) or defined amounts of in vitro transcript (also in hybridization buffer) is then combined with 5 μl of hybridization buffer containing 5×10$^5$ cpm of each antisense riboprobe in 0.5 ml EPPENDORF tubes, overlaid with 25 μl mineral oil, and hybridization accomplished by heating overnight at 55° C. The hybridization reactions are diluted into 0.5 ml RNAse solution (20 U/ml RNAse A, 2 U/ml RNAse T1, 10 U/ml RNAse-free DNAse I in 0.4 M NaCl), heated for 30 minutes at 37° C., and 10 μl of 20% SDS and 10 μl of Proteinase K (10 mg/ml) added, followed by an additional 30 minutes incubation at 37° C. Hybrids are partially purified by extraction with 0.5 ml of a 1:1 mixture of phenol/chloroform; aqueous phases are combined with 0.5 ml isopropanol, and RNAse-resistant hybrids pelleted for 10 minutes at room temperature (about 20° C.) in a microcentrifuge. Pellets are dissolved in 10 μl loading buffer (95% formamide, 1× TBE, 0.1% bromophenol blue, 0.1% xylene cylanol), heated to 95° C. for five minutes, cooled on ice, and analyzed on 4% polyacrylamide/7 M urea gels under denaturing conditions.

Ribozyme Stability

The chosen ribozyme can be tested to determine its stability, and thus its potential utility. Such a test can also be used to determine the effect of various chemical modifications (e.g., addition of a poly(A) tail) on the ribozyme stability and thus aid selection of a more stable ribozyme. For example, a reaction mixture contains 1 to 5 pmoles of 5' (kinased) and/or 3' labeled ribozyme, 15 μg of cytosolic extract and 2.5 mM MgCl$_2$ in a total volume of 100 μl. The reaction is incubated at 37° C. Eight μl aliquots are taken at timed intervals and mixed with 8 μl of a stop mix (20 mM EDTA, 95% formamide). Samples are separated on a 15% acrylamide sequencing gel, exposed to film, and scanned with an Ambis.

A 3'-labeled ribozyme can be formed by incorporation of the $^{32}$P-labeled cordycepin at the 3' OH using poly(A) polymerase. For example, the poly(A) polymerase reaction contains 40 mM Tris, pH 8, 10 mM MgCl$_2$, 250 mM NaCl, 2.5 mM MnCl$_2$,; 3 μl P$^{32}$ cordycepin, 500 Ci/mM; and 6 units poly(A) polymerase in a total volume of 50 μl. The reaction mixture was incubated for 30 minutes at 37° C.

Effect of Base Substitution upon Ribozyme Activity

To determine which primary structural characteristics could change ribozyme cleavage of substrate, minor base changes can be made in the substrate cleavage region recognized by a specific ribozyme. For example, the substrate sequences can be changed at the central "C" nucleotide, changing the cleavage site from a GUC to a GUA motif. The $K_{cat}/k_m$ values for cleavage using each substrate are then analyzed to determine if such a change increases ribozyme cleavage rates. Similar experiments can be performed to address the effects of changing bases complementary to the ribozyme binding arms. Changes predicted to maintain strong binding to the complementary substrate are preferred. Minor changes in nucleotide content can alter ribozyme/substrate interactions in ways which are unpredictable based upon binding strength alone. Structures in the catalytic core region of the ribozyme recognize trivial changes in either substrate structure or the three dimensional structure of the ribozyme/substrate complex.

To begin optimizing ribozyme design, the cleavage rates of ribozymes containing varied arm lengths, but targeted to the same length of short RNA substrate can be tested. Minimal arm lengths are required and effective cleavage varies with ribozyme/substrate combinations.

The cleavage activity of selected ribozymes can be assessed using HSV-homologous substrates. The assays are performed in ribozyme excess and approximate $K_{cat}/K_{min}$ values obtained. Comparison of values obtained with short and long substrates indicates utility in vivo of a ribozyme.

Intracellular Stability of Liposome-delivered Ribozymes

To test the stability of a chosen ribozyme in vivo the following test is useful. Ribozymes are $^{32}$P-end labeled, entrapped in liposomes and delivered to HSV sensitive cells for three hours. The cells are fractionated and purified by phenol/chloroform extraction. Cells (1×10$^7$, T-175 flask) are scraped from the surface of the flask and washed twice with cold PBS. The cells are homogenized by douncing 35 times in 4 ml of TSE (10 mM Tris, pH 7.4, 0.25 M Sucrose, mM EDTA). Nuclei are pelleted at 100×g for 10 minutes. Subcellular organelles (the membrane fraction) are pelleted at 200,000×g for two hours using an SW60 rotor. The pellet is resuspended in 1 ml of H buffer (0.25 M Sucrose, 50 mM HEPES, pH 7.4). The supernatant contains the cytoplasmic fraction (in approximately 3.7 ml). The nuclear pellet is resuspended in 1 ml of 65% sucrose in TM (50 mM Tris, pH 74., 2.5 mM MgCl$_2$) and banded on a sucrose step gradient (1 ml nuclei in 65% sucrose TM, 1 ml 60% sucrose TM, 1 ml 55% sucrose TM, 50% sucrose TM, 300 ul 25% sucrose TM) for one hour at 37,000×g with an SW60 rotor. The nuclear band is harvested and diluted to 10% sucrose with TM buffer. Nuclei are pelleted at 37,000×g using an SW60 rotor for 15 minutes and the pellet resuspended in 1 ml of TM buffer. Aliquots are size fractionated on denaturing polyacrylamide gels and the intracellular localization determined. By comparison to the migration rate of newly synthesized ribozyme, the various fraction containing intact ribozyme can be determined.

To investigate modifications which would lengthen the half-life of ribozyme molecules intracellularly, the cells may be fractioned as above and the purity of each fraction assessed by assaying enzyme activity known to exist in that fraction.

The various cell fractions are frozen at −70° C. and used to determine relative nuclease resistances of modified ribozyme molecules. Ribozyme molecules may be synthesized with 5 phosphorothioate (ps), or 2'-O-methyl (2'-OMe) modifications at each end of the molecule. These molecules and a phosphodiester version of the ribozyme are end-labeled with $^{32}$P and ATP using T4 polynucleotide kinase. Equal concentrations are added to the cell cytoplasmic extracts and aliquots of each taken at 10 minute intervals. The samples are size fractionated by denaturing PAGE and relative rates of nuclease resistance analyzed by scanning the gel with an Ambis β-scanner. The results show whether the ribozymes are digested by the cytoplasmic extract, and which versions are relatively more nuclease resistant. Modified ribozymes generally maintain 80–90% of the catalytic activity of the native ribozyme when short RNA substrates are employed.

Unlabeled, 5' end-labeled or 3' end-labeled ribozymes can be used in the assays. These experiments can also be performed with human cell extracts to verify the observations.

EXAMPLE 3

Delivery of Stable Ribozyme Into Vero Cells

Ribozymes were end-labeled, encapsulated in liposomes and delivered to Vero cells as described above. Intracellular ribozymes were purified from cell fractions by phenol/chloroform extraction, and aliquots were size fractionated along with newly synthesized ribozyme samples on denaturing polyacrylamide gels to determine intracellular location of intact ribozymes. By comparison with the migration rate of newly synthesized ribozymes, only the cytoplasmic fraction was observed to contain intact ribozyme. Although intact ribozymes recovered from the cytoplasmic fraction represented a relatively small percentage of the ribozymes encapsulated into the liposome preparations, these results demonstrate that ribozymes can be delivered to and retain stability within the cell cytoplasm via a liposome delivery vehicle.

EXAMPLE 4

Synthesis of Modified Ribozymes with Enhanced Resistance to Nuclease Digestion Modified ribozymes were synthesized with 5 phosphorothioate (PS) or 2' O-methyl (2' O-Me) modifications at each end of the molecule, and end-labeled with $^{32}P$-γATP using T4 polynucleotide kinase. Unmodified (phosphodiester) ribosomes were synthesized as described above, and similarly end-labeled.

Cultured Vero cells were fractionated as described above. The purity of each fraction was assessed by assaying enzyme activities known to reside in that fraction. As shown in Table IV, all enzyme activities tested were found predominantly in the appropriate cell fractions, indicating an acceptable level of purity. Cell fractions were frozen at −70° C. prior to use in a nuclease resistance assay.

TABLE IV

| | % OF TOTAL ENZYME ACTIVITY | | |
|---|---|---|---|
| ENZYME | Membrane Fraction | Nuclear Fraction | Cytoplasmic Fraction |
| Lactate Dehydrogenase (cytoplasmic marker) | 3 | 3 | 94 |
| Calcine (membrane marker) | 81 | 3 | 16 |
| Lysosome Hexosaminidase | 75 | 5 | 20 |
| Glucocerebrosidase (membrane marker) | 96 | 0 | 4 |
| Endosome Alkaline Phosphodiesterase (membrane marker) | 97 | 2 | 1 |

Equal concentrations (1–2 pmoles/100 microliters) of unmodified and PS or 2' O-Me modified ribozymes were added to Vero cell cytoplasmic extracts and incubated at 37° C. for 0–60 minutes. Aliquots of each were taken at 10 minute intervals, and size fractionated by electrophoresis on denaturing polyacrylamide gels (15%). Relative rates of ribozyme degradation were analyzed by scanning the gels with an Ambis beta scanner as measure of relative nuclease resistance.

We found that the unmodified ribozyme is quickly digested by the cytoplasmic extract, but that the PS and 2' O-Me modified ribozymes are not digested as rapidly and are thus relatively more nuclease resistant. The PS and 2' O-Me modified ribozymes retain 80–90% of the catalytic activity observed with their unmodified ribozyme counterparts, are better able to resist nuclease digestion, and therefore may have increased half-lifes in vivo. In that connection, PS and 2' O-Me modified ribozymes may have advantages over unmodified ribozymes for use in therapeutic applications.

In addition, we found that nearly equivalent nuclease resistance assay results were obtained for unlabeled, 5' end-labeled and 3' end-labeled unmodified ribozymes indicating that the observed loss of radioactive label in the PS and 2' O-Me modified ribozymes was not due to dephosphorylation of the 5' end labels, but instead reflects degradation by cytoplasmic nuclease. This suggests that a significant component of Vero cell nuclease activity is endonucleolytic in nature, and it may therefore be desirable to introduce similar modifications to the internal regions of the ribozyme molecule in order to best optimize nuclease resistance.

EXAMPLE 5

Ribozyme Cleavage of Single Base-Substituted Substrates In Vitro

Unmodified ribozymes I and E, specific for targets within the ICP4 gene of HSV-1, were synthesized and purified as described above.

A single nucleotide change was incorporated into the substrate cleavage site recognized by ribozyme I. Specifically, the substrate sequence CCGGGGGUCU-UCGCGCG was changed at the central C nucleotide to become CCGGGGGUAUUCGCGCG, so that the GUC cleavage site became GUA. This modified substrate was synthesized and tested for in vitro cleavage by ribozyme I using the ribozyme cleavage assay described above.

Single nucleotide changes were incorporated into the regions complementary to the ribozyme binding arms in the substrate RNAs recognized by ribozymes I and E as indicated in Table V, infra. Computer analysis of ribozyme/substrate folding predicted that these changes would result in the maintenance of ribozyme/substrate binding strength. Four such modified substrates were synthesized and tested alongside their "native" substrate counterparts for in vitro cleavage by ribozymes I or E.

Ribozyme I was tested for its ability to cleave two substrate sequences differing by a single base in the substrate cleavage site, one substrate corresponding to nucleotides 3550–3566 of the ICP4 mRNA sequence, and the other corresponding to the same sequence with a single base substitution in the cleavage site. The $k_{cat}/k_m$ values for cleavage of both substrates are $5.3 \times 10^7$ $M^{-1}$ $min^{-1}$ and $7.3 \times 10^7$ $M^{-1}$ $min^{-1}$ for the native and modified site respectively. The results indicate that ribozyme I is significantly more efficient at cleaving the modified substrate containing the GUA site. Thus, ribozyme I is not only capable of recognizing and cleaving the "native" ICP4 mRNA target, but is also capable of recognizing and cleaving (more efficiently) that same ICP4 mRNA target with a point mutation in the cleavage site. Natural mutations to particular cleavage sites in viral RNA within infected host cells are possible. Ribozyme I, therefore, may be a particularly good therapeutic ribozyme given its target recognition versatility. The results also suggest that ICP4 mRNA targets containing a GUA cleavage site would be acceptable if not preferred ribozyme substrates.

Ribozymes I and E were also tested for their ability to cleave substrates with single nucleotide modifications in the complementary regions. The results, shown in Table V, indicate that both ribozymes can recognize and efficiently cleave substrates with nucleotide point mutations. The results also show that relatively minor changes in substrate sequence can influence ribozyme/substrate interactions in ways that were not predicted based on binding strength alone.

TABLE V

EFFECT OF SUBSTRATE COMPLEMENTARY
REGION MODIFICATIONS ON RIBOZYME CATALYTIC ACTIVITY

| RIBO-ZYME | SUBSTRATE SEQUENCE | PREDICTED BINDING ENERGY (kcal/mole) | $k_{cat}/k_m$ $M^{-1}$ $min^{-1}$ |
|---|---|---|---|
| I | CCGGGGGUCUUCGCGCG | −13.3 | $5.3 \times 10^7$ |
|   | CCUGGGGUCUUCGCGCG | −10.9 | $3.3 \times 10^7$ |
|   | CCGGAGGUCUUCGCGCG | −5.3 | $7.5 \times 10^6$ |
| E | GAUGGCGUCGGAGAACA | −11.8 | $3 \times 10^7$ |
|   | GAUGGCGUCGGAGAUCA | −11.2 | $3.2 \times 10^7$ |
|   | GAUGGCGUCGGAAAACA | −8.0 | $2.9 \times 10^7$ |

Single base changes are indicated in boldface.

EXAMPLE 6

Effect of Ribozyme Arm Length on Cleavage Activity

Variations of ribozymes E and I having longer binding arm lengths were designed, synthesized and tested together with their prototype ribozymes for cleavage of the substrate recognized by the prototypes using a ribozyme cleavage assay.

The results are summarized in Table VI, and indicate that the minimal binding arm lengths required for effective cleavage vary from one ribozyme to another. This indicates that each chosen ribozyme will need to be optimized in its structure on an individual basis.

TABLE VI

EFFECT OF RIBOZYME BINDING STEM
LENGTH UPON SUBSTRATE CLEAVAGE

| Ribozyme | Hybridizing Stem Length (stem I, stem III) | Binding energy (kcal/mole) | $k_{cat}/k_m$ |
|---|---|---|---|
| E-32 | 5,5 | −9.1 | $3.8 \times 10^7$ $M^{-1}$ $min^{-1}$ |
| E-33–65 | 6,5 | −9.7 | $2.8 \times 10^7$ $M^{-1}$ $min^{-1}$ |
| E-33–56 | 5,6 | −11.2 | [NA] |
| E-34 | 6,6 | −11.8 | $3 \times 10^7$ $M^{-1}$ $min^{-1}$ |
| I-32 | 5,5 | −9.4 | $1.6 \times 10^7$ $M^{-1}$ $min^{-1}$ |
| I-33–65 | 6,5 | −10.1 | $<<1 \times 10^6$ $M^{-1}$ $min^{-1}$ |
| I-33–56 | 5,6 | −12.8 | $1 \times 10^6$ $M^{-1}$ $min^{-1}$ |
| I-34 | 6,6 | −13.3 | $5 \times 10^7$ $M^{-1}$ $min^{-1}$ |

NA = not available.

EXAMPLE 7

We have used the ribonuclease protection assay to determine the localization of the HSV ICP4 and ICP27 mRNAs within infected Vero cells. We found that >80% of the viral mRNAs were situated in the cytoplasm of the infected cells at 4 hours post infection. We have chosen a site within the HSV ICP4 mRNA which is accessible in RNAse H assays for further study. We have examined the effects of altering ribozyme binding arm lengths on catalytic activity and chosen a ribozyme which has binding arms of 6 nucleotides. We call this molecule RPI 1197. (See, Draper, "Constructs for High Yield Ribozyme Production", filed on the same day as the present application, hereby incorporated by reference herein.) We have checked the ability of RPI 1197 to cleave the ICP4 mRNA in cell lysates from infected cells and found that the amount of ICP4 cleaved by added RPI 1197 increased over time and gave the anticipated cleavage products. Using a liposome formulation which delivers ribozymes to the cytoplasm of cells, we pre-treated cells with two ribozyme molecules (RPI 1197 and RPI 1200 [a 2'-O-Methyl substituted version of 1197]) and tested them for their ability to reduce intracellular levels of the viral ICP4 mRNA and inhibit viral replication. We found that RPI 1197 and RPI 1200 reduced the mRNA levels by 10 and 36%, respectively, and viral load by 6 and 18%, respectively.

Early testing of the accessible sites of the UL5 transcript using the RNAse H assay has demonstrated that a number of regions within the transcript are accessible to binding of ribozymes. We have used a 622 nucleotide region (region D) of the UL5 RNA to check the cleavage ability of ribozymes targeted to both weakly and strongly accessible sites. We have found that the ribozyme activity in this fragment of RNA showed a good correlation between accessibility of sites and the ability of ribozymes to cleave the target RNA at those sites. In preliminary experiments, we have observed that the results of the RNAse H assay can also be mimicked using a gel-binding assay in which pieces of complementary nucleic acid (either RNA or DNA) are bound to target RNA and the mixtures are electrophoresed through gels to observe the formation of oligo/target complexes. By varying the concentration of the oligonucleotide, one can determine the accessible regions of the RNA as well as the binding affinity of the oligonucleotide for that region. We have found a good correlation between the strength of the binding complexes at particular sites and the activity of ribozymes at those sites within the UL5 RNA molecules.

Administration of Ribozyme

Selected ribozymes can be administered prophylactically, or to virus infected patients, e.g., by exogenous delivery of the ribozyme to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of ribozymes are also suitable.

The specific delivery route of any selected ribozyme will depend on the use of the ribozyme. Generally, a specific delivery program for each ribozyme will focus on naked ribozyme uptake with regard to intracellular localization, followed by demonstration of efficacy. Alternatively, delivery to these same cells in an organ or tissue of an animal can be pursued. Uptake studies will include uptake assays to evaluate cellular oligonucleotide uptake, regardless of the delivery vehicle or strategy. Such assays will also determine the intracellular localization of the oligonucleotide following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:
a. encapsulation in liposomes,
b. transduction by retroviral vectors,
c. conjugation with cholesterol,
d. localization to nuclear compartment utilizing antigen binding site found on most snRNAs,
e. neutralization of charge of ribozyme by using nucleotide derivatives, and
f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes and antisense oligonucleotides, like most small molecules, are taken up by cells, albeit slowly. To enhance cellular uptake, the ribozyme may be modified essentially at random, in ways which reduces its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell.

A liposome formulation which can associate ribozymes with the surface of lymphocytes and macrophages is also useful. This will provide enhanced delivery to HSV-infected cells by taking advantage of the specificity of macrophage and lymphocyte immune recognition of infected cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration.

Intraperitoneal administration also leads to entry into the circulation with the molecular weight or size of the ribozyme-delivery vehicle complex controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

The chosen method of delivery will result in cytoplasmic accumulation in the afflicted cells and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

Other embodiments are within the following claims.

I claim:

1. An enzymatic RNA molecule which specifically cleaves RNA encoding herpes simplex virus-1 (HSV-1) RNA, wherein said enzymatic RNA molecule comprises a substrate binding site and a nucleotide sequence within or surrounding said substrate binding site wherein said nucleotide sequence imparts to said enzymatic RNA molecule activity for the cleavage of said HSV-1 RNA.

2. The enzymatic RNA molecule of claim 1, wherein said HSV-1 RNA is encoded by genes selected from the group consisting of ICP0, ICP4, ICP22, ICP27, UL5, UL8, UL9, UL30, UL42, UL53, G.B. and GC.

3. The enzymatic RNA molecule of claim 1, wherein said substrate binding site is complementary to said HSV-1 RNA.

4. The enzymatic RNA molecule of claim 1, wherein said enzymatic RNA molecule is in a hammerhead motif.

5. The enzymatic RNA molecule of claim 1, wherein said enzymatic RNA molecule is in a hairpin motif.

6. The enzymatic RNA molecule of claim 1, wherein said substrate binding site comprises between 12 and 100 nucleotides complementary to said HSV-1 RNA.

7. The enzymatic RNA molecule of claim 1, wherein said substrate binding site comprises between 14 and 24 nucleotides complementary to said HSV-1 RNA.

8. An expression vector comprising a nucleic acid sequence encoding one or more enzymatic RNA molecules of claim 1 in a manner which allows expression of said enzymatic RNA molecules.

9. The expression vector of claim 8, wherein said expression vector is a viral vector.

10. The expression vector of claim 9, wherein said viral vector is a retrovirus vector.

11. The enzymatic RNA molecule of claim 1, wherein said enzymatic RNA molecule is chemically synthesized.

12. The enzymatic RNA molecule of claim 1, wherein said enzymatic RNA molecule is in a purified form.

13. The enzymatic RNA molecule of claim 1, wherein said enzymatic RNA molecule is active in the presence of divalent metal ions.

14. The enzymatic RNA molecule of claim 13, wherein said divalent metal ion is magnesium.

15. The enzymatic RNA molecule of claim 1, wherein said enzymatic RNA molecule comprises a ribose modification.

16. The expression vector of claim 8, wherein said nucleic acid sequence encoding said enzymatic RNA molecule is under the control of a mammalian transcription promoter.

17. The expression vector of claim 16, wherein said mammalian transcription promoter is a cytomegalovirus promoter.

18. The enzymatic RNA molecule of claim 1, wherein said enzymatic RNA molecule comprises a 5'-cap.

19. The enzymatic RNA molecule of claim 1, wherein said enzymatic RNA molecule comprises a 3'-cap.

20. The enzymatic RNA molecule of claim 1, wherein said enzymatic RNA molecule comprises a 3'-polyA tail.

21. A method of cleaving HSV-1 RNA comprising the step of contacting said HSV-1 RNA with the enzymatic RNA molecule of claim 1 under conditions suitable for the cleavage of said HSV-1 RNA.

* * * * *